United States Patent [19]

Clark

[11] Patent Number: 4,960,891
[45] Date of Patent: Oct. 2, 1990

[54] PROCESS FOR THE PREPARATION OF DECAHYDRO-8H-ISOQUINO[2,1-g][1,6]NAPHTHYRIDINE DERIVATIVES

[75] Inventor: Robin D. Clark, Palo Alto, Calif.

[73] Assignee: Syntex (U.S.A.) Inc., Palo Alto, Calif.

[21] Appl. No.: 336,993

[22] Filed: Apr. 11, 1989

Related U.S. Application Data

[63] Continuation-in-part of Ser. No. 257,372, Nov. 12, 1988, which is a continuation-in-part of Ser. No. 174,750, Mar. 29, 1988, Pat. No. 4,886,798, which is a continuation-in-part of Ser. No. 37,320, Apr. 13, 1987, Pat. No. 4,791,108.

[51] Int. Cl.$^5$ .......................................... C07D 455/03
[52] U.S. Cl. ...................................... 546/48; 544/125; 544/361; 546/70
[58] Field of Search .................. 544/125, 361; 546/48, 546/70

[56] References Cited

U.S. PATENT DOCUMENTS

| | | | |
|---|---|---|---|
| 3,210,357 | 10/1965 | Taylor et al. | 546/48 |
| 3,478,051 | 11/1969 | Houlihan | 546/70 |
| 3,850,936 | 11/1974 | Herbst | 546/70 |
| 3,953,598 | 4/1976 | Hall | 514/285 |
| 4,076,820 | 2/1978 | Archibald et al. | 546/95 |
| 4,316,028 | 2/1982 | Katsube et al. | 546/70 |
| 4,353,911 | 10/1982 | Buzas | 514/285 |
| 4,454,114 | 6/1986 | Ward et al. | 546/95 |
| 4,550,114 | 10/1985 | White | 514/294 |
| 4,706,682 | 2/1978 | Archibald et al. | 546/95 |
| 4,791,108 | 12/1988 | Clark | 546/70 |

FOREIGN PATENT DOCUMENTS

| | | | |
|---|---|---|---|
| 0288196 | 10/1988 | European Pat. Off. | 546/70 |
| 1064585 | 4/1967 | United Kingdom | 546/70 |

OTHER PUBLICATIONS

Investigation on the Chemistry of Berbans, by Lajor Szabo, et al, Nouv. J. Chim. 4(3), 199–202.

*Primary Examiner*—Donald G. Daus
*Attorney, Agent, or Firm*—Brian Lewis; Tom M. Moran

[57] ABSTRACT

The invention provides a process for preparing compounds, as a single enantiomer or mixture of enantiomers, represented by the formula:

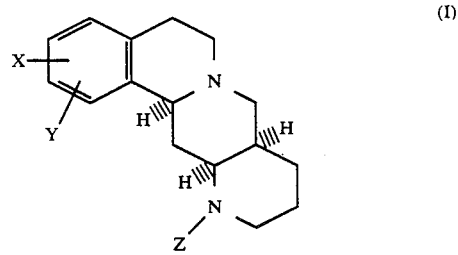

in which:

X and Y are independently hydrogen, hydroxy, lower alkyl, lower alkoxy or halo, or X and Y taken together is methylenedioxy or ethylene-1,2-dioxy, and Z is —SO$_2$R or —C(O)NR$^3$R$^4$, in which;

R is lower alkyl, optionally substituted phenyl, —(CH$_2$)$_m$OR$^1$ or —NR$^1$R$^2$ wherein m is an integer of 1 to 6 and R$^1$ and R$^2$ are independently hydrogen or lower alkyl; and R$^3$ and R$^4$ are independently hydrogen, alkyl, optionally substituted phenyl or phenyl lower alkyl; or R$^1$ and R$^2$ taken together with the nitrogen to which they are attached or R$^3$ and R$^4$ taken together with the nitrogen to which they are attached represent a heterocycle of the formula:

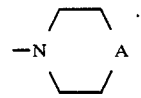

wherein A is —CH$_2$—, —NR$^1$— or oxygen; and novel intermediates.

29 Claims, No Drawings

PROCESS FOR THE PREPARATION OF DECAHYDRO-8H-ISOQUINO[2,1-g][1,6]NAPHTHYRIDINE DERIVATIVES

This is a continuation-in-part of U.S. patent application Ser. No. 257,372, filed Nov. 12, 1988, which is a continuation-in-part of U.S. patent application Ser. No. 174,750, filed Mar. 29, 1988, U.S. Pat. No. , 4,886,798, a continuation-in-part of U.S. patent application Ser. No. 037,320, filed Apr. 13, 1987, now issued as U.S. Pat. No. 4,791,108. Benefit of foreign priority is also claimed, based on European Patent Application 288,196, filed on Apr. 12, 1988. The complete disclosures of the above patent and patent applications are hereby incorporated by reference.

BACKGROUND OF THE INVENTION

1. Field of the Invention

The invention relates to a process, and the intermediates useful in such a process, for the preparation of decahydro-8H-isoquino[2,1-g][1,6]naphthyridine derivatives, as a single enantiomer or mixture of enantiomers. Such compounds exhibit selective $\alpha_2$-blockade in mammals, and are therefore useful as medicaments for the treatment of physiological conditions affected by such selective blockade.

2 Previous Disclosures

Processes for the preparation of various decahydro-8H-isoquino[2,1-g][1,6]naphthyridine derivatives, as a single enantiomer or mixture of enantiomers, were disclosed in U.S. patent application Ser. Nos. 174,750 and 257,372, and U.S. Pat. application Ser. No. 037,320 now issued as U.S. Pat. No. 4,791,108. The processes disclosed therein for the preparation of compounds of formula (I) utilize a common intermediate of formula:

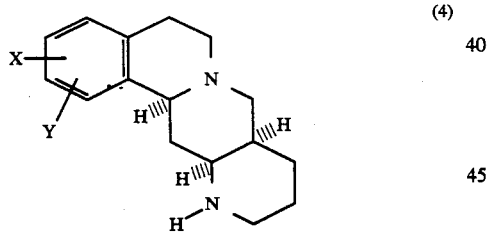

(4)

The intermediate of formula (4) is obtained as an oily, amorphous solid which is difficult to isolate or purify by recrystallization; purification requires the extra steps of conversion to its hydrochloride salt, recrystallization of the salt, and conversion back to the free base for the next reaction. In contrast the present process affords an intermediate of formula (3) (shown infra) which is highly crystalline, and is thus easily isolated, purified and manipulated on a large scale.

Surprisingly, it has also been found that reduction of the —C=O group seen at the 8-position of a compound of formula (3) to —CH$_2$ can be accomplished without concomitant reduction of other reactive sites of the molecule (in particular the 12-sulfonyl group and the 12-aminocarbonyl group), giving a compound of formula (I) in substantially pure form.

SUMMARY OF THE INVENTION

In a first aspect the present invention provides a process for the preparation of compounds, as a single enantiomer or mixture of enantiomers, represented by the formula:

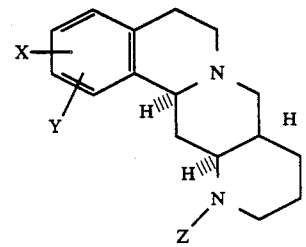

(I)

in which:
X and Y are independently hydrogen; hydroxy; lower alkyl of one to six carbon atoms; lower alkoxy of one to six carbon atoms; or halo; or X and Y taken together is methylenedioxy or ethylene-1,2 dioxy, and Z is —SO$_2$R or —C(O)NR$^3$R$^4$, in which;
R is lower alkyl of one to six carbon atoms; phenyl optionally substituted by one or two substituents chosen from halo, amino, lower alkyl of one to four carbon atoms and lower alkoxy groups of one to four carbon atoms; —(CH$_2$)$_m$OR$^1$; or —NR$^1$R$^2$; wherein m is an integer of 1 to 6 and R$^1$ and R$^2$ are independently hydrogen or lower alkyl; and R$^3$ and R$^4$ are independently hydrogen, alkyl of one to eight carbon atoms; phenyl or phenyl lower alkyl in which any phenyl group may be optionally substituted by one or two substituents chosen from halo, lower alkyl of one to four carbon atoms and lower alkoxy of one to four carbon atoms; or R$^1$ and R$^2$ taken together with the nitrogen to which they are attached or R$^3$ and Rtaken together with the nitrogen to which they are attached represent a heterocycle of the formula:

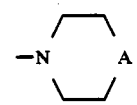

wherein A is —CH$_2$—, —NR$^1$— or oxygen; and includes the following reaction steps:

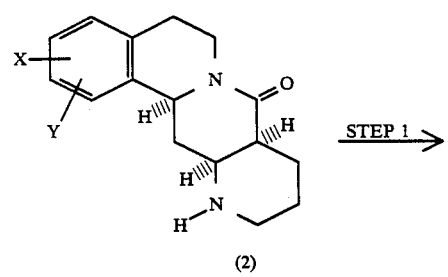

(2)

STEP 1

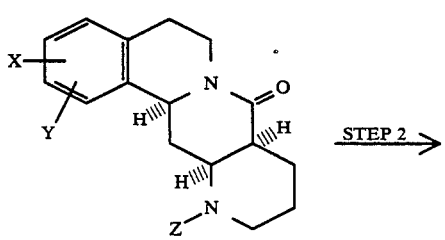

(3)

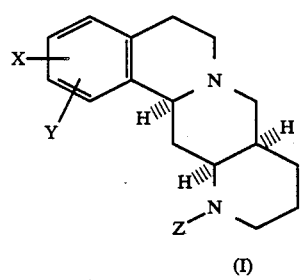

(I)

in which X, Y and Z are as defined above.

A second aspect of the invention relates to the novel intermediates of formula (3).

DETAILED DESCRIPTION OF THE INVENTION

Definitions

As used herein:

"Alkyl" means a branched or unbranched saturated hydrocarbon chain containing 1 to 8 carbon atoms, such as methyl, ethyl, propyl, tert-butyl, n-hexyl, n-octyl and the like;

"Lower alkyl" means a branched or unbranched saturated hydrocarbon chain containing 1 to 6 carbon atoms, such as methyl, ethyl, propyl, isopropyl, tert-butyl, butyl, n-hexyl and the like, unless otherwise indicated, for example phenyl optionally substituted by lower alkyl groups of one to four carbon atoms "Lower alkoxy" means the group —O—(lower alkyl) wherein lower alkyl is as herein defined.

"Cycloalkyl" as used herein means a saturated monovalent monocyclic hydrocarbon radical containing 3–8 carbon atoms, such as cyclopropyl, cyclobutyl, cyclopentyl, cyclohexyl, cycloheptyl and cyclooctyl.

"Halo" means fluoro, chloro, bromo and iodo.

"Phenyl" as used herein encompasses all possible isomeric phenyl radicals optionally monosubstituted or disubstituted with a substituent selected from the group consisting of lower alkyl, lower alkoxy, —NH$_2$, hydroxy, trifluoromethyl and halo.

"Phenyl lower alkyl" as used herein denotes phenyl as defined above attached to a lower alkyl group as defined above.

"Reducing agent" as used herein refers to an agent capable of selectively reducing the —C=O group found at the 8 position of a compound of formula (3) to —CH$_2$ without reacting with other reactive sites of the molecule Included in this definition are reducing agents such as, for example, lithium aluminum hydride, borane, triethyloxonium fluoroborate followed by sodium borohydride, sodium borohydride in the presence of a carboxylic acid, and the like. Preferred is sodium borohydride in the presence of boron trifluoride etherate.

"Optional" or "optionally" means that the subsequently described event or circumstance may or may not occur, and that the description includes instances where said event or circumstance occurs and instances in which it does not. For example, "optionally substituted phenyl" means that the phenyl may or may not be substituted and that the description includes both unsubstituted phenyl and substituted phenyl; "optionally followed by converting the free base to the acid addition salt" means that said conversion may or may not be carried out in order for the process described to fall within the invention, and the invention includes those processes wherein the free base is converted to the acid addition salt and those processes in which it is not.

The terms "α and β" indicate the specific stereochemical configuration of a substituent at an asymmetric carbon atom in a chemical structure as drawn. Thus "α", denoted by a broken line, indicates that the group at the position in question is below the general plane of the molecule as drawn, and "β", denoted by a bold line, indicates that the group at the position in question is above the general plane of the molecule as drawn.

The compounds represented by the structure (I) include each of the individual enantiomers depicted below as (Ia) and (Ib).

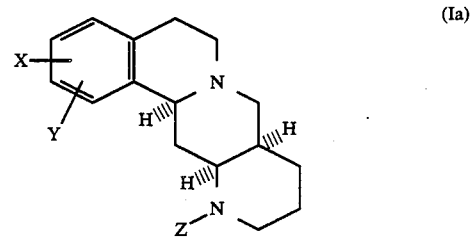

(Ia)

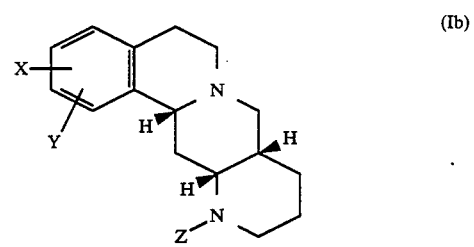

(Ib)

The term "(±)" is used to designate a racemic mixture of the individual enantiomers (Ia) and (Ib). The process for the preparation of the (±) racemate as well as the process for the preparation of the individual enantiomers of formula (Ia) and (Ib) and non-racemic mixtures thereof are included within the scope of this invention. The compounds represented by the formula (3) likewise include each of the individual enantiomers and racemic and non-racemic mixtures thereof.

Alternatively, the absolute stereochemistry at carbons 8a, 12a and 13a is specified according to the Cahn Ingold-Prelog R-S system. When the compound is a pure enantiomer the stereochemistry at each chiral carbon may be specified by either R or S. When a compound is a racemic mixture the stereochemistry at each chiral carbon may be specified by either RS or SR by reference to a single enantiomer of the racemate. In this manner relative stereochemistry is conveyed unambiguously.

"Isomers" are different compounds that have the same molecular formula.

"Stereoisomers" are isomers that differ only in the way the atoms are arranged in space.

"Enantiomers" are a pair of stereoisomers that are non-superimposable mirror images of each other. A 1:1 mixture of a pair of enantiomers is a "racemic" mixture.

The compounds of the invention will be named using the numbering system shown below.

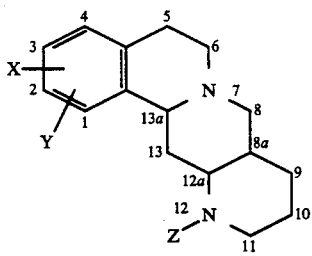

Following are examples of how representative compounds are named:

One optically active isomer of formula (I) wherein X is 3-methoxy, Y is hydrogen and Z is —SO$_2$R, where R is methyl, is named:

(8aR,12aS,13aS)-3 methoxy-12-methanesulfonyl-5,6,8a,9,10,11,12,12a,13,13a-decahydro-8H-isoquino[2,1-g][1,6]naphthyridine. A racemic compound of formula (3) wherein X is 3-methoxy, Y is hydrogen and and Z is —C(O)NR$_3$R$_4$, in which R$_3$ and R$_4$ are both methyl, is named:

(±) -3-methoxy-12-(N,N-dimethylamino)carbonyl-5,6, 8a,α, 9,10,11,12,12aα, 13,13aα-decahydroisoquino[2,2-g][1,6]naphthyridin-8-one.

The compounds of formula (I) prepared by the present process are useful for the treatment of disease states which include, but are not limited to, depression, anxiety, excessive platelet aggregation, diabetes, elevated intraocular pressure, male impotence, irritable bowel syndrome, hypertension, obesity, shortened recovery from anasthesia and cyclic mood disturbances in females.

The present process is illustrated in more detail in Reaction Scheme I.

REACTION SCHEME I

REACTION SCHEME I

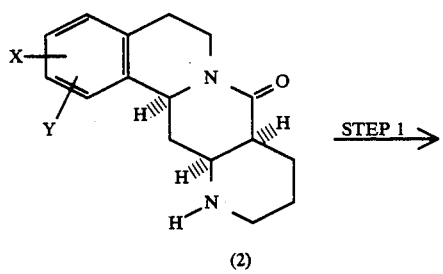

-continued
REACTION SCHEME I

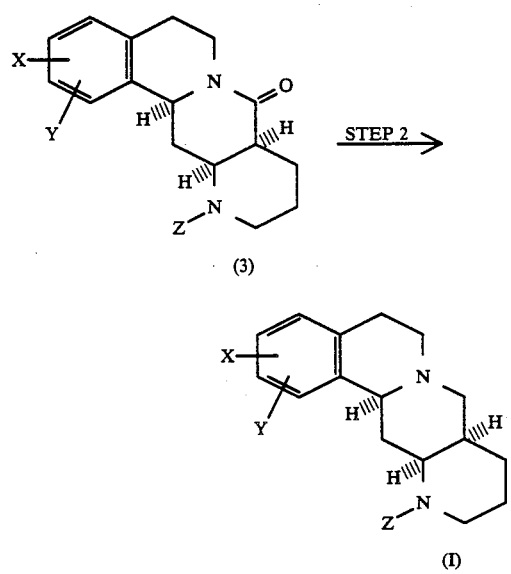

The starting compound represented by the formula (2) is obtained as a racemic mixture as shown in U.S. patent application Ser. No. 037,320, now issued as U.S. Pat. No. 4,791,108, or as either of the individual enantiomers as shown in U.S. patent application Ser. No. 174,750.

The reaction of Step 1 in its broadest aspect comprises the reaction of a compound of the formula (2) with a compound of the formula ZV, where Z is as defined above and V is a leaving group. Where ZV is a substituted sulfonyl halide of the formula VSO$_2$R, where R is as defined above, V is preferably chlorine or bromine, where ZV is a compound of the formula VC(O)NR$^3$R$^4$, in which R$^3$ and R$^4$ are as defined above but are not hydrogen, V is preferably chlorine. The sulfonyl halides of formula VSO$_2$R are either commercially available from, inter alia, Aldrich Chemical Co., or may be prepared according to the method of Zeigler and Sprague, disclosed in J. Org. Chem., Vol 16, p 621 (1951). The carbamyl chlorides of formula R$^3$R$^4$NC(O))Cl are either commercially available from, inter alia, Aldrich Chemical Co., or may be prepared by methods well known in the art.

Typically the compound of formula (2) is dissolved in an inert organic solvent, such as benzene, toluene, ethyl acetate, tetrahydrofuran, diethyl ether, chloroform or preferably dichloromethane, containing from 1–10 molar equivalents, preferably about 2 molar equivalents, of an inorganic base such as sodium carbonate, potassium bicarbonate or the like, or preferably a tertiary organic base, such as pyridine, N-methylpiperidine and the like, preferably triethylamine. The mixture is cooled to about −10° to 10° C., preferably about 0° C., and about 1–4 molar equivalents, preferably about 1.5 molar equivalents, of the appropriately substituted sulfonyl halide of formula VSO$_2$R added and the mixture stirred for about 10 minutes to 2 hours, preferably about 30 minutes at a temperature of about 10° to 40° C., preferably about 25° C. When the reaction is substantially complete, the compound of formula (3) where Z is —SO$_2$R is isolated by conventional means, and purified by, for example, chromatography or crystallization from an inert solvent Alternatively, the mixture of the compound of formula (2) and base as above is cooled to about 0° to 40° C., preferably about 25° C., and about 1-4 molar equivalents, preferably about 1.1 molar equivalents, of the appropriately substituted compound of formula $R^3R^4NC(O)Cl$ added and the mixture stirred for about 5-30 hours, preferably about 16 hours. When the reaction is substantially complete, the compound of formula (3) where Z is —$C(O)NR^3R^4$ is isolated by conventional means, and purified by, for example, chromatography or crystallization from an inert solvent.

Alternatively, the compounds of formula (3) where Z is —$C(O)NR^3R^4$, where $R^3$ is hydrogen and $R^4$ is other than hydrogen, may be prepared by reacting the compound of formula (2) with an isocyanate of the formula $R^4NCO$. Typically, the compound of formula (2) is dissolved in an inert solvent as defined above, preferably toluene, and reacted with from 1 to 1.5 molar equivalents, preferably about 1.0 molar equivalents, of the compound of formula $R^4NCO$. The reaction is carried out at a temperature of about 0°-40° C., preferably about 25°, for about 5-30 hours, preferably about 16 hours. When the reaction is substantially complete, the product of formula (3) where Z is —$C(O)NHR^4$ is isolated and purified by conventional means, preferably chromatography The compounds of formula (3) where Z is —$C(O)NH_2$ are prepared by reacting the compound of formula (2) with potassium isocyanate in the presence of an acid, preferably acetic acid.

Alternatively, the compounds of formula (3) where Z is —$C(O)NR^3R^4$ may be prepared by first reacting the compound of formula (2) with phosgene, then reacting the resultant carbamoyl chloride with an amine of formula $HNR^3R^4$. For example, the compound of formula (2) is reacted with from 1-10 molar equivalents, preferably about 2 molar equivalents, of phosgene in an inert organic solvent as defined above, preferably benzene. The reaction takes place in the presence of from 1-5 molar equivalents, preferably about 2 molar equivalents of a tertiary organic base such as triethylamine or preferably pyridine. The reaction is conducted at from 0°-50° C., preferably about 25° C., for about 1-48 hours, preferably about 16 hours, and then filtered. To the filtrate is added from 1-5 molar equivalents, preferably about 2 molar equivalents of an organic base of the formula $HNR^3R^4$, and the mixture stirred at about 0°-50° C., preferably about 25° C., for about 1-12 hours, preferably about 2 hours. When the reaction is substantially complete, the product of formula (3) where Z is —$C(O)NR^3R^4$ is isolated and purified by conventional means, preferably chromatography.

The reaction of Step 2 in its broadest aspect comprises the reaction of a compound of the formula (3) with a reducing agent to give a compound of formula (I). Suitable reducing agents include, for example, lithium aluminum hydride, borane, triethyloxonium fluoroborate followed by sodium borohydride, sodium borohydride in the presence of a carboxylic acid, or preferably sodium borohydride in the presence of boron trifluoride etherate. Typically, a mixture is prepared of the compound of formula (3) and about 2 to 8 molar equivalents, preferably about 4 molar equivalents, of sodium borohydride in an ethereal solvent, for example diethyl ether, dimethoxyethane, dioxane, or preferably tetrahydrofuran. The mixture is cooled to about 0° to 0° C., preferably about 10° C., and about 2 to 10 molar equivalents, preferably about 6 molar equivalents, of boron trifluoride etherate is added. The mixture is then refluxed for about 15 minutes to 4 hours, preferably about 45 minutes. When the reaction is substantially complete, the compound of formula (I) is separated and purified by conventional means, for example by recrystallization of an acid salt.

The following examples illustrate the invention but are not intended to limit its scope.

EXAMPLE 1

Preparaton of (8aS,12aS, 13aS)-3-methoxy-12-methanesulfonyl-5,6,8a,9,10,11,12,12a,13,13a-decahydro isoquino[2,1g][1,6]naphthyridin-8-one and Related Compounds of Formula (3) where Z is —$SO_2R$ A. A solution of 11 g of (8aS, 12aS, 13As)-3-methoxy-5,6,-8a,9,10,11,12,12a,13,13a-decahydroisoquino[2,1-g][1,6]naphthyridin-8-one (2) in 300 ml of methylene chloride and 10 ml of triethylamine was cooled in an ice bath and 5 ml of methanesulfonyl chloride was added. The mixture was stirred at room temperature for 30 minutes, diluted with 100 ml of hexane, and extracted with water. The organic layer was dried over sodium sulfate and the solvent removed under reduced pressure. The residue was crystallized from isopropanol, to give 11 g of (8aS,12aS,13aS)-3-methoxy-12-methanesulfonyl 5,6,8a,9,10,11,12,12a,13,13a-decahydroisoquino[2,1-g][1,6]naphthyridin-8-one, m.p. 138°-140° C.

B. Similarly, replacing (8aS,12aS,13aS)-3-methoxy-5,6,8a,9,10,11,12,12a,13,13a-decahydroisoquino[2,1-g][1,6]naphthyridin-8-one with (8aS,12aS,13aS)-2,3-methylenedioxy-5,6,8a,9,10,11,12,12a,13,13a-decahydroisoquino[2,1-g][1,6]naphthyridin-8-one, the following compound was made:

(8aS,12aS,13aS)-2,3-methylenedioxy-12-methanesulfonyl-5,6,8a,9,10,11,12,12a,13,13a-decahydroisoquino[2,1-g][1,6]naphthyridin-8-one, m.p. 262°-263° C.

C. Similarly, replacing (8aS,12aS,13aS)-3-methoxy-5,6,8a,9,10,11,12,12a,13,13a-decahydroisoquino[2,1-g][1,6]naphthyridin-8-one with (8aR,12aR,13aR)-3-methoxy-5,6,8a,9,10,11,12,12a,13,13a-decahydroisoquino[2,1-g][1,6]naphthyridin-8-one, the following compound is made:

(8aR,12aR,13aR)-3-methoxy-12-methanesulfonyl-5,6,8a,9,10,11,12,12a,13,13a-decahydroisoquino[2,1-g][1,6]- naphthyridin-8 one.

D. Similarly, replacing (8aS,12aS,13aS)-3-methoxy-5,6,8a,9,10,11,12,12a,13,13a-decahydroisoquino[2,1-g][1,6]naphthyridin-8-one with (±)-3-methoxy-5,6,8aα,9,10,11,12,12aα,13,13a-decahydroisoquino[2,1-g][1,6]naphthyridin-8-one or (±)-2,3-methylenedioxy-5,6,8aα,9,10,11,12,12aα,13,13aα-decahydroisoquino-[2,1-g][1,6]naphthyridin-8-one, the following compounds are made:

(±)-3 methoxy-12-methanesulfonyl-5,6,8aα,9,10,11,12,12aα,13,13α-decahydroisoquino[2,1-g][1,6]-naphthyridin 8-one; and (±)-2,3-methylenedioxy- 12-methanesulfonyl-5,6,8aα,9,10,11,12,12aα,13,13α-decahydroisoquino[2,1-g][1,6]naphthyridin-8-one.

E. Similarly, optionally replacing (8aS,12aS,13aS)-3-methoxy-5,6,8a,9,10,11,12,12a,13,13a-decahydroisoquino-[2,1-g][1,6]naphthyridin-8-one with other compounds of formula (2), as the individual enantiomers or racemic or non-racemic mixtures thereof, optionally replacing methanesulfonyl chloride with other sulfonyl halides of formula VSO$_2$R and following the procedure in paragraph A above, following compounds of formula (3) where Z is—SO$_2$R, as either of the individual enantiomers or racenic or non racemic mixtures thereof, are made:

12-methanesulfonyl-5,6,8a$\alpha$,9,10,11,12,12a$\alpha$, 13,13a$\alpha$-decahydroisoquino[2,1-g][1,6]naphthyridin-8-one;

12-ethanesulfonyl 5,6,8a$\alpha$,9,10,11,12,12a$\alpha$, 13,13a$\alpha$decahydroisoquino[2,1-g][1,6]naphthyridin 8-one, 12-(1 propanesulfonyl)-5,6,8a$\alpha$,9,10,11,12,12a$\alpha$,13,-13a$\alpha$-decahydroisoquino[2,1-g][1,6]naphthyridin-8-one, 12-(1-butanesulfonyl)-5,6,8a$\alpha$,9,10,11,12,12$\alpha$, a$\alpha$,-decahydroisoquino[2,1-g][1,6]naphthyridin 8 one;

(2-methylpropanesulfonyl) 5,6,8a$\alpha$,9,10,11,12,-12$\alpha$,13,13a$\alpha$-decahydroisoquino[2,1-g][1,6]naphthyridin-8-one;

12-phenylsulfonyl 5,6,8a$\alpha$,9,10,11,12,12a$\alpha$,1-3,a$\alpha$decahydroisoquino[2,1 g][1,6]naphthyridin 8-one;

12-(4-methoxyphenylsulfonyl)-5,6,8a$\alpha$, 9,10,11,12,12$\alpha$; 13,13a$\alpha$-decahydroisoquino[2,1 g][1,6]- naphthyridin-8-one;

12-(4 chlorophenylsulfonyl)-5,6,8a$\alpha$,9,10,11,12,13,-13a$\alpha$-decahydroisoquino[2,1-g][1,6]naphthyridin-8one;, (4-fluorophenylsulfonyl)-5,6,8a$\alpha$,9,10,11,12,12a$\alpha$, 13,13a$\alpha$-decahydroisoquino[2,1-g][1,6]naphthyridin 8-one;

12-(2 methoxyethanesulfonyl)-5,6,8a$\alpha$, 9,10,11,12a$\alpha$, 13,13a$\alpha$-decahydroisoquino[2,1 g][1,6]naphthyridin 8one;

3-methoxy 12-ethanesulfonyl-5,6,8a$\alpha$,9,10,11,12,-12a$\alpha$, 13,13a$\alpha$-decahydroisoquino[2,1 g][1,6]naphthyridin 8-one;

methoxy-12 (1 propanesulfonyl) 5,6,8a$\alpha$, 9,10,11,12,12a$\alpha$, 13,13a$\alpha$-decahydroisoquino[2,1-g][1,6]-naphthyridin-8-one;

3-methoxy 12-phenylsulfonyl 5,6,8a$\alpha$, 9,10,11,12,-12a$\alpha$, 13, 13a$\alpha$-decahydroisoquino[2,1-g][1,6]-naphthyridin-8-one;

3-methoxy 12-(2-methylpropanesulfonyl)-5,6,8a$\alpha$,9,10,11,12,12a$\alpha$,13,13a$\alpha$-decahydroisoquino[2,1-g][1,6]naphthyridin-8-one;

3methoxy-12-(1-piperazinosulfonyl)-5,6,8a$\alpha$,9,10,11,12,12a$\alpha$,13,13a$\alpha$-decahydroisoquino[2,1 g][1,6]naphthyridin-8-one;

3-methoxy-12-(1 morpholinosulfonyl) 5,6,8a$\alpha$,9,10, 11,12,12a$\alpha$,13,13a$\alpha$-decahydroisoquino[2,1g][1,6-]naphthyridin 8-one;

3 methoxy 12-(1 piperidinosulfonyl) 5,6,8a$\alpha$, 9,10,11,12,12a$\alpha$,13,13a$\alpha$-decahydroisoquino[2,1g][1,6]naphthyridin-8-one;

2,3-dimethoxy-12-methanesulfonyl 5,6,8a$\alpha$,9,10,11,12,12a$\alpha$,13,13a$\alpha$-decahydroisoquino[2,1-g][1,6]naphthyridin 8-one;

1,4 dimethoxy 12 methanesulfonyl 5,6,8a$\alpha$, 9,10,11,12,12a$\alpha$,13,13a$\alpha$- decahydroisoquino[2,1-g][1,6]naphthyridin-8-one;

2,3-dimethoxy 12-(2 methylpropanesulfonyl)-5,6, 8a$\alpha$,9,10,11,12,12a$\alpha$,13,13a$\alpha$-decahydroisoquino [2,1 g][1,6]naphthyridin-8-one;

2,3 methylenedioxy-12-methanesulfonyl-5,6,8a$\alpha$, 9,10,11,12,12a$\alpha$,13,13a$\alpha$-decahydroisoquino[2,1 g][1,6]naphthyridin-8-one;

2,3-(ethylene 1,2 dioxy) 12 methanesulfonyl 5,6, 8a$\alpha$,9,10,11,12,12a$\alpha$,13,13a$\alpha$-decahydroisoquino[2,1-g][1,6]naphthyridin-8-one;

2,3 methylenedioxy 12-(2-methylpropanesulfonyl)-5,6,8a$\alpha$,9,10,11,12,12a$\alpha$,13,13a$\alpha$-decahydroisoquino [2,1g][1,6]naphthyridin 8-one;

3 methoxy-12-(2-methoxyethanesulfonyl) 5,6,8a$\alpha$,9,10,11,12,12a$\alpha$,13,13a$\alpha$-decahydroisoquino[2,1g][1,6]-naphthyridin-8-one;

12(4-aminophenylsulfonyl)-5,6,8a$\alpha$, 9,10,11,12,12a$\alpha$, 13,13a$\alpha$-decahydroisoquino[2,1-g][1,6]-naphthyridin-8-one;

12-(2-hydroxyethanesulfonyl)-5,6,8a$\alpha$, 9,10,11,12,12a$\alpha$,13,13a$\alpha$-decahydroisoquino[2,1-g][1,6]-naphthyridin-8-one;

1-methyl-12 methanesulfonyl- 5,6,8a$\alpha$, 9,10,11,12,12a$\alpha$,13,13a$\alpha$-decahydroisoquino[2,1-g][1,6]naphthyridin-8-one;

2-methyl-12-methanesulfonyl-5,6,8a$\alpha$,9,10,11,12,-12a$\alpha$,13,13a$\alpha$-decahydroisoquino[2,1-g][1,6]naphthyridin-8-one;

3-methyl-12-methanesulfonyl 5,6,8a$\alpha$, 9,10,11,12,12a$\alpha$,13,13a$\alpha$-decahydroisoquino[2,1-g][1,6]naphthyridin-8one;

3-ethyl 12 methanesulfonyl-5,6,8a$\alpha$,9,10,11,12,12 a$\alpha$,13,13a$\alpha$-decahydroisoquino[2,1-g][1,6]-naphthyridin-8-one;

2,3dimethyl-12-methanesulfonyl-5,6,8a$\alpha$,9,10,11,12,-12a$\alpha$,13,13a$\alpha$-decahydroisoquino[2,1-g][1,6]naphthyridin-8-one;

3-isobutyl 12 methanesulfonyl-5,6,8a$\alpha$,9,10,11,12,-12a$\alpha$,13,13a$\alpha$-decahydroisoquino[2,1-g][1,6]-naphthyridin-8-one;

2-n hexyl-12-methanesulfonyl-5,6,8a$\alpha$, 9,10,11,12,12a$\alpha$,13,13a$\alpha$-decahydroisoquino[2,1g][1,6]naphthyridin- 8-one;

3 methoxy-2-methyl-12-methanesulfonyl- 5,6,8a$\alpha$,9,10,11,12,12a$\alpha$,13,13a$\alpha$-decahydroisoquino[2,1 g][1,6]naphthyridin -8-one;

1-methoxy-12 methanesulfonyl-5,6,8a$\alpha$,9,10,11,12,-12a$\alpha$,13,13a$\alpha$-decahydroisoquino[2,1g][1,6]naphthyridin-8-one;

2 methoxy-12-methanesulfonyl 5,6,8a$\alpha$,9,10,11,12,-12a$\alpha$,13,13a$\alpha$-decahydroisoquino[2,1-g][1,6]naphthyridin-8one;

4 methoxy 12-methanesulfonyl-5,6,8a$\alpha$,9,10,11,12,-12a$\alpha$, 13,13a$\alpha$-decahydroisoquino[2,1-g][1,6]naphthyridin-8-one;

3-ethoxy-12-methanesulfonyl-5,6,8a$\alpha$,9,10,11,12,-12a$\alpha$,13,13a$\alpha$-decahydroisoquino[2,1-g][1,6]-naphthyridin-8-one;

3-ethoxy 12 ethanesulfonyl-5,6,8a$\alpha$, 9,10,11,12,12a$\alpha$,13,13a$\alpha$-decahydroisoquino[2,1g][1,6]naphthyridin-8-one;

3-isopropoxy-12-methanesulfonyl-5,6,8a$\alpha$, 9,10,11,12,12a$\alpha$, 13,13a$\alpha$, -decahydroisoquino[2,1-g][1,6]- naphthyridin-8-one;

3-isobutoxy-12-methanesulfonyl-5,6,8a$\alpha$,9,10,11,12,-12a$\alpha$, 13,13a$\alpha$-decahydroisoquino[2,1-g][1,6]-naphthyridin-8-one;

3-n-hexyloxy-12-methanesulfonyl-5,6,8a$\alpha$,9,10,11,12,12a$\alpha$, 13,13a$\alpha$-decahydroisoquino[2,1-g][1,6]-naphthyridin-8-one;

3-hydroxy 12 methanesulfonyl-5,6,8aα,9,10,11,12,-12aα, 13,13aα-decahydroisoquino[2,1 g][1,6]naphthyridin-8-one;

2,3-dihydroxy-12 methanesulfonyl-5,6,8aα, 9,10,11,12,12aα,13,13aα-decahydroisoquino[2,1-g][1,6]naphthyridin-8-one;

2,3-dimethoxy-12-methanesulfonyl 5,6,8aα, 9,10,11,12,12aα,13,13aα-decahydroisoquino[2,1-g][1,6]naphthyridin-8-one, 2,3-diethoxy-12-methanesulfonyl-5,6,8aα, 9,10,11,12,12aα,13,13aα-decahydroisoquino[2,1-g][1,6]naphthyridin-8-one;

2,3 di-n-butoxy-12-methanesulfonyl-5,6,8aα, 9,10,11,12,12aα,13,13aα-decahydroisoquino[2,1-g][1,6]-naphthyridin-8-one;

3,4-methylenedioxy-12-methanesulfonyl-5,6,8aα, 9, 10,11,12,12aα,13,13aα-decahydroisoquino[2,1-g][1,6]naphthyridin-8-one;

2 chloro-12 methanesulfonyl-5,6,8aα,9,10,11,12,-12aα,13,13aα-decahydroisoquino[2,1g][1,6]naphthyridin-8-one;

3 chloro-12-methanesulfonyl-5,6,8aα,9,10,11,12,12aα, 13,13aα-decahydroisoquino[2,1-g][1,6]naphthyridin 8-one;

2 fluoro-12-methanesulfonyl-5,6,8aα,9,10,11,12,-12aα,13,13aα-decahydroisoquino[2,1-g][1,6]naphthyridin-8one;

3-fluoro 12-methanesulfonyl 5,6,8aα,9,10,11,12,-12aα,13,13aα-decahydroisoquino[2,1-g][1,6]naphthyridin-8one;

12 aminosulfonyl 5,6,8aα,9,10,11,12,12aα, 13,aα-decahydroisoquino[2,1g][1,6]-naphthyridin 8-one;

3 methoxy 12 aminosulfonyl-5,6,8aα,9,10,11,12,-12aα,13,13aα-decahydroisoquino[2,1-g][1,6]naphthyridin 8-one;

12-methylaminosulfonyl 5,6,8aα,9,10,11,12,12aα, 13,13aα-decahydroisoquino[2,1g][1,6]naphthyridin-8-one; 12-diethylaminosulfonyl-5,6,8aα,9,10,11,12,12aα, 13,13aα-decahydroisoquino[2,1-g][1,6]naphthyridin 8-one; 12 di-n-hexylaminosulfonyl 5,6,8aα,9,10,11,12 aα,13,-13aα-decahydroisoquino[2,1-g][1,6]naphthyridin-8-one;

12 (1 piperazinosulfonyl)-5,6,8aα,9,10,11,12,12 aα,13,13aα-decahydroisoquino[2,1g][1,6]naphthyridin-8-one;

12-(1-morpholinosulfonyl) 5,6,8aα,9,10,11,12,-12aα,13,13aα-decahydroisoquino[2,1-g][1,6]naphthyridin-8-one;

12 (1-piperidinosulfonyl)-5,6,8aα,9,10,11,12,12aα,13,-13aα-decahydroisoquino[2,1-g][1,6]naphthyridin-8-one;

3-methyl-12 ethanesulfonyl-5,6,8aα, 9,10,11,12, 12aα,13,13aα-decahydroisoquino[2,1-g][1,6]-naphthyridin-8one;

3-ethoxy 12 ethanesulfonyl-5,6,8aα, 9,10,11,12,12aα,13,13aα-decahydroisoquino[2,1-g][1,6]- naphthyridin-8-one;

3-n-hexyloxy-12-ethanesulfonyl-5,6,8aα, 9,10,11,12,12aα,13,13aα-decahydroisoquino[2,1-g][1,6]naphthyridin-8-one;

2,3-diethoxy-12 ethanesulfonyl-5,6,8aα,9,10,11,12,-12aα,13,13aα-decahydroisoquino[2,1-g][1,6]naphthyridin-8-one;

3-methyl-12-(1-n-hexylsulfonyl)-5,6,8aα, 9,10,11,12,12aα,13,13aα-decahydroisoquino[2,1 g][1,6]naphthyridin-8-one;

3-methoxy 12-(1 n-hexanesulfonyl) 5,68aα,9,10,11,12,12aα,13,13aα-decahydroisoquino[2,1-g][1,6]-naphthyridin-8-one;

2,3 dimethoxy 12 (1-n hexanesulfonyl) 5,6,8aα,9, 10,11,12,12aα,13,13aα-decahydroisoquino[2,1-g][1,6]naphthyridin-8-one;

3 methoxy-12 phenylsulfonyl 5,6,8aα,9,10,11,12,-12aα,13,13aα-decahydroisoquino[2,1 g][1,6]-naphthyridin-8-one;

3-methoxy12(N,N-dimethylaminosulfonyl)-5,6,8aα,9,10,11,12,12aα,13,13aα-decahydroisoquino[2,1 g][1,6]naphthyridin-8-one;

3-methoxy-12-(t-butylaminosulfonyl)-5,6,8aα, 9,10,11,12,12aα,13,13aα-decahydroisoquino[2,1g][1,6]naphthyridin-8-one;

2,3-dimethoxy-12-(N,N-dimethylaminosulfonyl)-5,6, 8aα,9,10,11,12,12aα,13,13aα-decahydroisoquin-[2,1g][1,6]naphthyridin-8-one;

2,3-methylenedioxy-12-(N,N-dimethylaminosulfonyl)-5,6,8aα,9,10,11,12,12aα,13,13aα-decahydroisoquino- [2,1-g][1,6]naphthyridin-8-one; and 2-methyl-12 (2-methoxymethanesulfonyl)-5,6,8aα, 9,10,11,12,12aα,13,13aα-decahydroisoquino[2,1-g][1,6]naphthyridin-8-one.

EXAMPLE 2

Preparation of (±)-12-N N Dimethylaminocarbonyl-5,6, 8α, 9,10,11,12,.12aα, b 13,13aα-decahydroisoquino[21G][1,6]naphthyridin-8one and Related Compounds of Formula (3) where Z is —C(O)NR³R⁴

A. A solution of 4.5 g of (±)-5,6,8aα9,10,11,12,-12aα,13,13aα-decahydroisoquino[2,1-g][1,6]naphthyridine (2) and 6.6 ml of triethylamine in 100 ml of methylene chloride is stirred at room temperature and 1.56 ml of dimethylcarbamyl chloride is added. The mixture is stirred at room temperature for 16 hours, then solvent removed under reduced pressure The residue is partitioned between 200 ml of methylene chloride and 50 ml of 2N sodium carbonate. The organic phase is dried over anhydrous magnesium sulfate, the solvent removed under reduced pressure, and the residue chromatographed on silica gel, eluting with 3% methanol/methylene chloride, to give (±)-12 N,N-dimethylaminocarbonyl-5,6,8aα, 9,10,11,12,12aα,13,13aα-decahydroisoquino[2,1-g][1,6]naphthyridin 8-one.

B. Similarly, optionally replacing (±)-5,6,8aα,9,10,11,12,12aα,13,13aα-decahydro-8H-isoquino[2,1-g][1,6]naphthyridine with the appropriate compound of formula (2), and optionally replacing dimethylcarbamyl chloride with other carbamyl chlorides of formula R³R⁴C(O)Cl, where R³ and R⁴ are as defined supra but are not hydrogen, and following the procedure in paragraph A above, the following compounds of formula (3) where Z is —C(O)NR³R⁴, as either of the individual enantiomers or racemic or nonracemic mixtures thereof, are made:

12 N,N- diethylaminocarbonyl-5,6,8aα,9,10,11,12,-12aα,13,13aα-decahydroisoquino[2,1-g][1,6]-naphthyridin-8-one;

3-methoxy-12-N,N-dimethylaminocarbonyl 5,6,8aα, 9,10,11,12,12aα,13,13a° -decahydroisoquino[2,1-g][1,6]naphthyridin-8-one;

2,3-methylenedioxy-12-N,N dimethylaminocarbonyl-5,6,8aα,9,10,11,12,12aα,13,13aα-decahydroisoquino[2,1 g][1,6]naphthyridin-8-one;

2,3-methylenedioxy-12-N,N-dimethylaminocarbonyl-5,6,8a,9,10,11,12,12a,13,13a-decahydroisoquino-[2,1g][1,6]naphthyridin 8-one;
3 methoxy-12 (pyrrolidin 1-yl)carbonyl 5,6,8aα,9,10,11,12,12aα,13,13aα-decahydroisoquino[2,1-g][1,6]naphthyridin-8-one;
3-methoxy-12 (4 methylpiperazin-1-yl)carbonyl-5,6,8aα,9,10,11,12,12aα,13,13aα-decahydroisoquino-[2,1-g][1,6]naphthyridin 8-one;
3methoxy-12 (morpholin-1-yl)carbonyl-5,6,8aα, 9,10,11,12,12aα,13,13aα-decahydroisoquino[2,1g][1,6]naphthyridin-8-one;
3methyl-12-N,N-dimethylaminocarbonyl-5,6,8aα, 9,10,11,12,12aα,13,13aα-decahydroisoquino[2,1-g][1,6]naphthyridin-8-one;
2,3dimethoxy-12-N,N-dimethylaminocarbonyl-5,6,8aα,9,10,11,12,12aα,13,13aα-decahydroisoquino-[2,1-g][1,6]naphthyridin 8-one;
12-N-methyl-N-ethylaminocarbonyl 5,6,8aα,9,10,11,12,12aα, 13,13aα-decahydroisoquino[2,1-g][1,6]naphthyridin 8-one;
12-N methyl N-butylaminocarbonyl 5,6,8aα, 9,10,11,12,12aα,13,13aα-decahydroisoquino[2,1-g][1,6]-naphthyridin-8-one;
12-N,N-di-n-hexylaminocarbonyl-5,6,8aα, 9,10,11,12,12aα,13,13aα-decahydroisoquino[2,1-g][1,6]naphthyridin-8one;
12-N,N-diphenylaminocarbonyl-5,6,8aα, 9,10,11,12,12aα,13,13aα-decahydroisoquino[2,1g][1,6]naphthyridin-8-one;
12-(pyrrolidin-1-yl)carbonyl-5,6,8aα,9,10,11,12,-12aα,13,13aα-decahydroisoquino[2,1-g][1,6]naphthyridin-8-one;
12-(4-methylpiperazin-1-yl)carbonyl-5,6,8aα,9,10,11,12,12aα,13,13aα-decahydroisoquino[2,1-g][1,6]naphthyridin-8-one;
12-(morpholin-1-yl)carbonyl-5,6,8aα,9,10,11,12,-12aα,13,13aα-decahydroisoquino[2,1-g][1,6]naphthyridin 8-one;
3-methoxy-12-N-methyl-N-ethylaminocarbonyl-5,6,8aα,9,10,11,12,12aα,13,13aα-decahydroisoquino [2,1-g][1,6]naphthyridin-8-one;
3methoxy-12-N-methyl-N-butylaminocarbonyl-5,6,8aα,9,10,11,12,12aα,13,13aα-decahydroisoquino[2,1-g][1,6]-naphthyridin-8-one;
3-methoxy-12-N,N-di-n-hexylaminocarbonyl-5,6,8aα,9,10,11,12,12aα,13,13aα-decahydroisoquino[2,1-g][1,6]naphthyridin-8-one;
3-methoxy-12-N,N-diphenylaminocarbonyl-5,6,8aα,9,10,11,12,12aα,13,13aα-decahydroisoquino[2,1-g][1,6]naphthyridin-8-one;
2,3methylenedioxy-12-N-methyl-N-ethylaminocarbonyl-5,6,8aα,9,10,11,12,12aα,13,13aα-decahydroisoquino[2,1-g][1,6]naphthyridin-8-one;
2,3-ethylenedioxy-12-N,N-dimethylaminocarbonyl-5,6,8aα,9,10,11,12,12aα,13,13aα-decahydroisoquino[2,1-g][1,6]naphthyridin-8-one;
2,3methylenedioxy-12-N-methyl-N-butylaminocarbonyl-5,6,8aα,9,10,11,12,12aα,13,13aα-decahydroisoquino[2,1-g][1,6]aphthyridin-8-one;
2,3-methylenedioxy-12-N,N-di-n-hexylaminocarbonyl-5,6,8aα,9,10,11,12,12aα,13,13aα-decahydroisoquino[2,1-g][1,6]naphthyridin-8-one;
2,3-methylenedioxy-12-N,N-diphenylaminocarbonyl-5,6,8aα,9,10,11,12,12aα,13,13aα-decahydroisoquino[2,1-g][1,6]naphthyridin-8-one;

2,3-methylenedioxy-12-(pyrrolidin-1-yl)carbonyl-5,6,8aα,9,10,11,12,12aα,13,13aα-decahydroisoquino[2,1-g][1,6]naphthyridin-8-one;
2,3-methylenedioxy-12-(4-methylpiperazin-1-yl) carbonyl-5,6,8aα,9,10,11,12,12aα,13,13aα-decahydro-8H-isoquino[2,1-g][1,6]naphthyridin-8-one;
2,3-methylenedioxy-12-(morpholin-1-yl)carbonyl-5,6,8aα,9,10,11,12,12aα,13,13aα-decahydroisoquino[2,1-g][1,6]naphthyridin-8-one;
2-methyl-12-N,N-dimethylaminocarbonyl-5,6,8aα,9,10,11,12,12aα,13,13aα-decahydroisoquino[2,1-g][1,6]naphthyridin-8-one;
2,3-dimethyl-12-N,N-dimethylaminocarbonyl-5,6,aα,9,10,11,12,12aα,13,13aα-decahydroisoquino[2,1-g][1,6]naphthyridin-8-one;
3-n-hexyl-12-N,N-dimethylaminocarbonyl-5,6,8aα,9,10,11,12,12aα,13,13aα-decahydroisoquino[2,1-g][1,6]naphthyridin-8-one;
2-methoxy-12-N,N-dimethylaminocarbonyl-5,6,8aα,9,10,11,12,12aα,13,13aα-decahydroisoquino[2,1-g][1,6]naphthyridin-8-one;
3-ethoxy-12-N,N-dimethylaminocarbonyl-5,6,8aα,9,10,11,12,12aα,13,13aα-decahydroisoquino[2,1-g][1,6]naphthyridin-8-one;
3-n-hexyloxy-12-N,N-dimethylaminocarbonyl-5,6,8aα,9,10,11,12,12aα,13,13aα-decahydroisoquino[2,1-g][1,6]naphthyridin-8-one;
3-hydroxy-12-N,N-dimethylaminocarbonyl-5,6,aα,9,10,11,12,12aα,13,13aα-decahydroisoquino[2,1-g][1,6]naphthyridin-8-one;
3,4-methylenedioxy-12-N,N-dimethylaminocarbonyl-5,6,8aα,9,10,11,12,12aα,13,13aα-decahydroisoquino[2,1-g][1,6]naphthyridin-8-one;
3-chloro-12-N,N-dimethylaminocarbonyl-5,6,8aα,9,10,11,12,12aα,13,13aα-decahydroisoquino[2,1-g][1,6]naphthyridin-8-one; and
3-fluoro-12-N,N-dimethylaminocarbonyl-5,6,8aα,9,10,11,12,12aα,13,13aα-decahydroisoquino[2,1-g][1,6]naphthyridin-8-one.

EXAMPLE 3

Preparation of (8aS,12aS,13aS)-3-methoxy-12-[(R)-(+)-1-phenylethylamino]carbonyl-5,6,8a,9,10,11,12,12a,13,13a-decahydroisoquino[2,1-g][1,6]naphthyridin-8-one and Related Compounds of Formula (3) where Z is —C(O)NHR$^4$ A. A solution of 1.95-g of (±)-3-methoxy-5,6,8aα,9,10,11,12,12aα,13,13aα-decahydroisoquino-[2,1-g][1,6]naphthyridin-8-one, a compound of formula (2), and 1.0-g of (R)-(+)-α-methylbenzyl isocyanate in 50 ml of methylene chloride was stirred at room temperature for 30 minutes. Solvent was then removed under reduced pressure, and the residue chromatographed on silica gel, using multiple medium pressure chromatography and eluting with 5% methanol in ethy acetate. The first compound eluted was (8aS,12aS,-13aS)-3-methoxy-12[(R)-(+)-1-phenylethylamino]carbonyl-5,6,8a,9,10,11,12,12a,13,13a-decahydroisoquino[2,1-g][1,6]naphthyridin-8-one, mp 198°–199° C., [α]$_D^{25}$=+36.5-(CHCl$_3$) )

B. Similarly, replacing (±)-3-methoxy-5,6,8aα,9,10,11,12,12aα,13,13aα-decahydroisoquino[2,1-g][1,6]naphthyridin-8-one with the appropriate compound of formula (2) and following the procedure in paragraph A above, the following compounds of formula (3) were prepared:

(8aS,12aS,13aS)-12-[(R)-(+)-1-phenylethylamino]-carbonyl-5,6,8a,9,10,11,12,12a,13,13a-decahydroisoquino[2,1-g][1,6]naphthyridin-8-one; and (8aS,12aS-13aS)-2,3-methylenedioxy-12-[(R) (+) 1-phenylethylamino]carbonyl-5,6,8a,9,10,11,12,-12a,13,13a-decahydroisoquino[2,1-g][1,6]naphthyridin-8-one.

C. Similarly, optionally replacing (±)-3-methoxy-5,6,8aα,9,10,11,12,12aα,13,13aα-decahydroisoquino[2,1-g][1,6]naphthyridin-8-one with the appropriate compound of formula (2), and optionally replacing (R)-(+)-α-methylbenzyl isocyanate with the appropriate compound of formula $R^4NCO$ and following the procedure in paragraph A above, the following compounds of formula (3) where Z is —C(O)NHR$^4$, as either of the individual enantiomers or racemic or non-racemic mixtures thereof, are prepared:

12-benzylaminocarbonyl-5,6,8aα,9,10,11,12,12aα,13,-13aα-decahydroisoquino[2,1-g][1,6]naphthyridin-8-one;

12-isopropylaminocarbonyl-5,6,8aα,9,10,11,12,-12aα,13,13aα-decahydroisoquino[2,1-g][1,6]naphthyridin-8-one;

12-n-butylaminocarbonyl-5,6,8aα,9,10,11,12,-12aα,13,13aα-decahydroisoquino[2,1-g][1,6]naphthyridin-8-one;

12-t-butylaminocarbonyl-5,6,8aα,9,10,11,12,12aα,13,-13aα-decahydroisoquino[2,1-g][1,6]naphthyridin-8-one;

3-methoxy-12phenylaminocarbonyl-5,6,8aα,9,10,11,12,12aα,13,13aα-decahydroisoquino[2,1-g][1,6]naphthyridin-8-one;

12-[(R)-(+)-1-phenylethylamino]carbonyl-5,6,8aα,9,10,11,12,12aα,13,13aα-decahydroisoquino[2,1-g][1,6]naphthyridin-8-one;

12[(R)-(+)-1-phenylethylamino]-carbonyl-5,6,8aα,9,10,11,12,12aα,13,13aα-decahydroisoquino[2,1-g][1,6]naphthyridin-8-one;

3-methoxy-12-[(R)-(+)-1-phenylethylamino]carbonyl-5,6,8aα,9,10,11,12,12aα,13,13aα-decahydroisoquino[2,1-g][1,6]naphthyridin-8-one;

12-ethylaminocarbonyl-5,6,8aα,9,10,11,12,12aα,13,-13aα-decahydroisoquino[2,1-g][1,6]naphthyridin-8-one;

12-n-butylaminocarbonyl-5,6,8aα,9,10,11,12,-12aα,13,13aα-decahydroisoquino[2,1-g][1,6]naphthyridin-8-one;

12-n-octylaminocarbonyl-5,6,8aα,9,10,11,12,-12aα, 13,13aα-decahydroisoquino[2,1-g][1,6]-naphthyridin-8-one;

12phenylaminocarbonyl-5,6,8aα,9,10,11,12,12aα,13,13aα-decahydroisoquino[2,1-g][1,6]naphthyridin-8-one., 3-methoxy-12-ethylaminocarbonyl-5,6,8aα,9,10,11,12,12aα,13,13aα-decahydroisoquino[2,1-g][1,6]naphthyridin-8-one;

3-methoxy-12-n-butylaminocarbonyl-5,6,8aα, 9,10,11,12,12aα,13,13aα-decahydroisoquino[2,1]-g][1,6]naphthyridin-8-one;

3-methoxy 12-n-octylaminocarbonyl-5,6,8aα,9,10,11,12,12aα,13,13aα-decahydroisoquino[2,1-g][1,6]naphthyridin-8-one;

3-methoxy-12-phenylaminocarbonyl-5,6,8aα, 9,10,11,12,12aα,13,13aα-decahydroisoquino[2,1-g][1,6]naphthyridin-8-one;

2,3-methylenedioxy-12-ethylaminocarbonyl-5,6,8aα, 9,10,11,12,12aα,13,13aα-decahydroisoquino [2,1-g][1,6]naphthyridin-8-one;

2,3-methylenedioxy-12-n-butylaminocarbonyl-5,6,8aα, 9,10,11,12,12aα,13,13aα-decahydroisoquino[2,1-g][1,6]naphthyridin-8-one;

2,3-methylenedioxy-12-n-octylaminocarbonyl-5,6,8aα,9,10,11,12,12aα,13,13aα-decahydroisoquino[2,1-g][1,6]naphthyridin-8-one;

2,3-methylenedioxy-12-phenylaminocarbonyl-5,6,8aα,9,10,11,12,12aα,13,13aα-decahydroisoquino[2,1-g][1,6]naphthyridin-8-one;

2,3-methylenedioxy-12-benzylaminocarbonyl-5,6,8aα,9,10,11,12,12aα,13,13aα-decahydroisoquino[2,1-g][1,6]naphthyridin-8-one;

2-methyl-12-benzylaminocarbonyl-5,6,8aα, 9,10,11,12,12aα,13,13aα-decahydroisoquino[2,1-g][1,6]-naphthyridin-8-one;

3-methyl-12-benzylaminocarbonyl-5,6,8aα, 9,10,11,12,12aα,13,13aα-decahydroisoquino[2,1-g][1,6]-naphthyridin-8-one;

2,3-dimethyl-12-benzylaminocarbonyl-5,6, 8aα, 9,10,12,12aα,13,13aα-decahydroisoquino[2,1-g][1,6]-naphthyridin-8-one, 3-n hexyl-12-benzylaminocarbonyl-5,6,8aα, 9,10,11,12,12aα,13,13aα-decahydroisoquino[2,1-g][1,6]-naphthyridin-8-one;

2-methoxy-12-benzylaminocarbonyl-5,6,8aα, 9,10,11,12,12aα,13,13aα-decahydroisoquino[2,1-g][1,6]naphthyridin-8-one;

3-ethoxy-12-benzylaminocarbonyl-5,6,8aα, 9,10,11,12,12aα,13,13aα-decahydroisoquino[2,1-g][1,6]-naphthyridin-8-one., 3-n-hexyloxy-12-benzylaminocarbonyl-5,6,8aα,9,10,11,12,12aα,13,13aα-decahydroisoquino[2,1-g][1,6]naphthyridin-8-one;

3-hydroxy-12-benzylaminocarbonyl-5,6,8aα,9,10,11,2,12aα,13,13aα-decahydroisoquino[2,1-g][1,6]naphthyridin-8-one;

2,3-dimethoxy-12-benzylaminocarbonyl-5,6,8aα, 9,10,11,12,12aα,13.13aα-decahydroisoquino[2,1-g][1,6]naphthyridin-8-one;

3,4-methylenedioxy-12-benzylaminocarbonyl 5,6,8aα, 9,10,11,12,12aα,13,13aα-decahydroisoquino [2,1-g][1,6]naphthyridin-8-one;

3-chloro-12-benzylaminocarbonyl-5,6,8aα,9,10,11,12,12aα,13,13aα-decahydroisoquino[2,1-g][1,6]naphthyridin-8-one; and 3-fluoro-12-benzylaminocarbonyl-5,6,8aα,9,10,11 12,12aα,13,13aα-decahydroisoquino[2,1-g][1,6]naphthyridin-8-one.

EXAMPLE 4

Preparation of (8aR,12aS,13aS)-3-methoxy-12-methanesulfonyl-5,6,8a,9,10,11,12,12a,13,13a-decahydro-8H-isoguino[2,1g][1,6]naphthyridine hydrochloride and Related Compounds of Formula (I)

A solution of 3.64-g of (8aS,12aS,13aS)-3-methoxy-12-methanesulfonyl-5,6,8a,9,10,11,12,12a,13,13a-decahydroisoquino[2,1-g][1,6]naphthyridin-8-one in 100 ml of tetrahydrofuran was stirred with 1.52-g of sodium borohydride. This mixture was cooled to 10° C. and 7.4 ml of boron trifluoride etherate added rapidly. The reaction mixture was refluxed for 45 minutes, cooled to 20° C., and 100 ml of 1N-hydrochloric acid added dropwise. The majority of the solvent was then removed by distillation at atmospheric pressure, the residue cooled to 30° C. and aqueous 6N-sodium hydroxide solution added until the pH reached 11–12. The reaction mixture was then extracted with methylene chloride, and the combined extracts washed with water and dried over sodium sulfate. The solvent was removed under reduced pressure, and the residue dissolved in about 150 ml of a mixture of 33% ethanol in methylene chloride, and the solution treated with a slight excess of hydrochloric acid in ethanol and filtered. The filtrate was concentrated at atmospheric pressure to a volume of about 50 ml, stirred at room temperature for 30 minutes and the precipitate filtered off, giving (8aR,12aS,13aS)-3-methoxy-12methanesulfonyl-5,6,8a,9,10,11,12,12a,13,13a-decahydro-8H-isoquino[2,1g][1,6]naphthyridine hydrochloride, m.p. 257°–258° C.

B. Similarly, replacing (8aS,12aS,13aS)-3-methoxy-12-methanesulfonyl-5,6,8a,9,10,11,12,12a,13,13a-decahydroisoquino[2,1-g][1,6]naphthyridin-8-one with (8aS,12aS,13aS)-2,3-methylenedioxy 12methanesulfonyl-5,6,8a,9,10,11,12,12a,13,13a-decahydroisoquino[2,1-g][1,6]naphthyridin-8-one, the following compound was made:

(8aR,12aS,13aS)-2,3-methylenedioxy-12methanesulfonyl-5,6,8a,9,10,11,12,12a,13,13a-decahydro 8H-isoquino[2,1g][1,6]naphthyridine hydrochloride, mp 263°–265° C.

C. Similarly, replacing (8aS,12aS,13aS)-3-methoxy-12-methanesulfonyl-5,6,8a,9,10,11,12,12a,13,13a-decahydroisoquino[2,1-g][1,6]naphthyridin-8-one with (8aR,12aR,13aR) 3-methoxy-12-methanesulfonyl 5,6,8a,9,10,11,12,12a,13,13a-decahydroisoquino[2,1-g][1,6]naphthyridin-8-one, the following compound is made:

(8aS,12aR,13aR)-3-methoxy-12-methanesulfonyl 5,6,8a,9,10,11,12,12a,13,13a-decahydro 8H-isoquino[2,1g][1,6]naphthyridine hydrochloride.

D. Similarly, replacing (8aS,12aS,13aS)-3methoxy-12-methanesulfonyl-5,6,8a,9,10,11,12,12a,13,13a-decahydroisoquino[2,1-g][1,6]naphthyridin-8-one with (±)-3-methoxy-12-methanesulfonyl-5,6,8aα,9,10,11,12,-12aα,13,13aα-decahydroisoquino[2,1-g][1,6]naphthyridin-8-one or (±)-2,3-methylenedioxy 12-methanesulfonyl-5,6,8aα,9,10,11,12,12aα,13,13aα-decahydroisoquino[2,1-g][1,6]naphthyridin-8-one, the following compounds are made:

(±)-3-methoxy-12-methanesulfonyl-5,6,8aα,9,10,11,12,12aα,13,13aα-decahydro-8H-isoquino[2,1g][1,6]naphthyridine hydrochloride; and (±)-2,3-methylenedioxy-12-methanesulfonyl-5,6,8aα,9,10,11,12,12aα,13,13aα-decahydro-8H-isoquino[2, 1g][1,6]naphthyridine hydrochloride.

E. Similarly, replacing (8aS,12aS,13aS)-3-methoxy-12-methanesulfonyl-5,6,8a,9,10,11,12,12a,13,13a decahydroisoquino[2,1-g][1,6]naphthyridin-8-one with other compounds of formula (3), as the individual enantiomers or racemic or non racemic mixtures thereof, and following the procedure in paragraph A above, the following compounds of formula (I), as the individual enantiomers or racemic or non-racemic mixtures thereof, are made as the hydrochloride salt:

12-methanesulfonyl-5,6,8aα,9,10,11,12,12aα,13,13aα-decahydro-8H-isoquino[2,1-g][1,6]naphthyridine;

12-ethanesulfonyl-5,6,8aα,9,10,11,12,12aα,13,decahydro-8H-isoquino[2,1-g][1,6]naphthyridine;

12-(1-propanesulfonyl)-5,6,8aα,9,10,11,12,12aα,13,-13aα-decahydro-8H-isoquino[2,1-g][1,6]naphthyridine;

12-(1-butanesulfonyl)-5,6,8aα,9,10,11,12,12aα,13,13aα-decahydro-8H-isoquino[2,1-g][1,6]naphthyridine;

12-(2-methylpropanesulfonyl)-5,6,8aα,9,10,11,12,13,13aα-decahydro-8H-isoquino[2,1-g][1,6]naphthyridine;

12-phenylsulfonyl-5,6,8aα,9,10,11,12,12aα,13,13aα-decahydro-8H-isoquino[2,1-g][1,6]naphthyridine;

12-(4-methoxyphenylsulfonyl)-5,6,8aα, 9,10,11,12aα,13,13aα-decahydro-8H-isoquino[2,1-g][1,6]naphthyridine;

12-(4-chlorophenylsulfonyl)-5,6,8aα,9,10,11,12,12aα,13,13aα-decahydro-8H-isoquino[2,1-g][1,6]naphthyridine;

12-(4-fluorophenylsulfonyl)-5,6,8aα,9,10,11,12,13,-13aα-decahydro-8H-isoquino[2,1-g][1,6]naphthyridine;

12-(2-methoxyethanesulfonyl)-5,6,8aα,9,10,11,12,13,-13aα-decahydro-8H-isoquino[2,1-g][1,6]naphthyridine;

3-methoxy-12-ethanesulfonyl-5,6,8aα,9,10,11,12,13,-13aα-decahydro-8H-isoquino[2,1-g][1,6]naphthyridine;

3-methoxy-12-(1-propanesulfonyl)-5,6,8aα,9,10,11,12,12aα,13,13aα-decahydro-8H-isoquino[2,1-g][1,6]naphthyridine;

3-methoxy-12-phenylsulfonyl-5,6,8aα,9,10,11,12,13,-13aα-decahydro-8H-isoquino[2,1-g][1,6]naphthyridine;

3-methoxy-12-(2-methylpropanesulfonyl)-5,6,8aα,9,10,11,12,12aα,13,13aα-decahydro-8H-isoquino [2,1-g][1,6]naphthyridine;

3-methoxy-12-(1-piperazinosulfonyl)-5,6,8aα, 9,10,11,12,12aα,13,13aα-decahydro-8H-isoquino[2,1-g][1,6]naphthyridine;

3-methoxy-12-(1-morpholinosulfonyl)-5,6,8aα,9,10,11,12,12aα,13,13aα-decahydro-8H-isoquino[2,1-g][1,6]naphthyridine;

3methoxy-12-(1-piperidinosulfonyl)-5,6,8aα,9,10,11,12,12aα,13,13aα-decahydro-8H-isoquino[2,1-g][1,6]naphthyridine;

2,3dimethoxy-12-methanesulfonyl 5,6,8aα,9,10,11,12,12aα,13,13aα-decahydro-8H-isoquino[2,1-g][1,6]naphthyridine;

1,4-dimethoxy12-methanesulfonyl-5,6,8aα,9,10,11,12,12aα,13,13aα-decahydro-8H-isoquino[2,1-g][1,6]naphthyridine., 2,3dimethoxy-12-(2-methylpropanesulfonyl)-5,6,9,10,11,12,12aα,13,13aα-decahydro-8H-isoquino[2,1-g][1,6]naphthyridine;

2,3-methylenedioxy-12-methanesulfonyl-5,6,8aα,9,10,11,12,12aα,13,13aα-decahydro-8H-isoquino[2,1-g][1,6]naphthyridine;

2,3-(ethylene-1,2-dioxy)-12-methanesulfonyl-5,6,9,10,11,12,12aα,13,13aα-decahydro-8H-isoquino[2,1-g][1,6]naphthyridine;

2,3-methylenedioxy-12-(2methylpropanesulfonyl)-5,6,9,10,11,12,12aα,13,13aα-decahydro-8H-isoquino[2,1-g][1,6]naphthyridine, 3-methoxy-12-(2-methoxyethanesulfonyl)-5,6,8aα,9,10,11,11,12,12aα,13,13aα-decahydro-8H-isoquino[2,1-g][1,6]naphthyridine;

12-(4-aminophenylsulfonyl)-5,6,8aα,9,10,11,12aα,13,13aα-decahydro-8H-isoquino[2,1-g][1,6]naphthyridine;

12-(2-hydroxyethanesulfonyl)-5,6,8aα,9,10,11,12,-12aα, 13,13aα-decahydro-8H-isoquino[2,1-g][1,6]naphthyridine;

1-methyl-12-methanesulfonyl-5,6,8aα,9,10,11,12,-12aα,13,13aα-decahydro-8H-isoquino[2,1-g][1,6]naphthyridine;
2-methyl-12-methanesulfonyl-5,6,8aα,9,10,11,12,-12aα, 13,13aα-decahydro-8H-isoquino[2,1-g][1,6]naphthyridine;
3-methyl-12-methanesulfonyl-5,6,8aα,9,10,11,12,-12aα,13,13aα-decahydro-8H-isoquino[2,1-g][1,6]naphthyridine;
3-ethyl-12-methanesulfonyl-5,6,8aα,9,10,11,12,12aα, 13,13aα-decahydro-8H-isoquino[2,1-g][1,6]naphthyridin;
2,3-dimethyl-12-methanesulfonyl-5,6,8aα,9,10,11,12,-12aα,13,13aα-decahydro-8H-isoquino[2,1-g][1,6]naphthyridine;
3-isobutyl-12-methanesulfonyl-5,6,8aα,9,10,11,12,-12aα, 13,13aα-decahydro 8H-isoquino[2,1-g][1,6]naphthyridine;
2-n-hexyl-12-methanesulfonyl-5,6,8aα,9,10,11,12,-12aα, 13,13aα-decahydro-8H-isoquino[2,1-g][1,6]naphthyridine;
3-methoxy-2-methyl-12-methanesulfonyl-5,6,8aα,9,10,11,12,12aα,13,13aα-decahydro 8H-isoquino[[2,1-g][1,6]naphthyridine;
1-methoxy-12-methanesulfonyl 5,6,8aα,9,10,11,12,13,13aα-decahydro-8H-isoquino[2,1-g][1,6]naphthyridine;
2-methoxy-12methanesulfonyl 5,6,8aα,12aα, 13,13aα-decahydro-8H-isoquino[2,1-g][1,6]naphthyridine;
-methoxy 12-methanesulfonyl-5,6,8aα,9,10,11,12,-12aα, 13,13aα-decahydro-8H-isoquino[2,1-g][1,6]naphthyridine;
3-ethoxy 12-methanesulfonyl-5,6,8aα,9,10,11,12,-12aα, 13,13aα-decahydro-8H-isoquino[2,1-g][1,6]naphthyridine;
3ethoxy-12-ethanesulfonyl-5,6,8aα,9,10,11,12,-12aα,13,13aα-decahydro-8H-isoquino[2,1-g][1,6]naphthyridine;
3-isopropoxy 12-methanesulfonyl-5,6,8aα,9,10,11,12,-12aα,13,13aα-decahydro-8H-isoquino[2,1-g][1,6]naphthyridine;
3-isobutoxy-12-methanesulfonyl-5,6,8aα,9,10,11,12,-12aα,13,13aα-decahydro-8H-isoquino[2,1-g][1,6]naphthyridine;
3-n-hexyloxy-12-methanesulfonyl-5,6,8aα,9,10,11,12,12aα,13,13aα-decahydro-8H-isoquino[2,1-g][1,6]naphthyridine;
-hydroxy-12-methanesulfonyl-5,6,8aα,3b 9,10,11,12,12aα,13,13aα-decahydro-8H-isoquino[2,1-g][1,6]naphthyridine;
2,3-dihydroxy-12-methanesulfonyl-5,6,8aα,9,10,11,12,12aα,13,13aα-decahydro-8H-isoquino[2,1-g][1,6]naphthyridine.,
1,2-dimethoxy 12-methanesulfonyl-5,6,8aα,9,10,11,12,12aα,13,13aα-decahydro-8H-isoquino[2,1-g][1,6]naphthyridine;
2,3-diethoxy 12-methanesulfonyl-5,6,8aα,9,10,11,12,-12aα,13,13aα-decahydro-8H-isoquino[2,1-g][1,6]naphthyridine;
2,3-di-n butoxy-12-methanesulfony-5,6,8aα,9,10,11,12,12aα,13,13aα-decahydro-8H-isoquino[2,1-g][1,6]naphthyridine;
3,4-methylenedioxy-12-methanesulfonyl-5,6,8aα,9,10,11,12,12aα,13,13aα-decahydro-8H-isoquino [2,1-g][1,6]naphthyridine;
2-chloro 12-methanesulfonyl-5,6,8aα,9,10,11,12-12aα,13,13aα-decahydro-8H-isoquino[2,1-g][1,6]naphthyridine;
3-chloro 12methanesulfonyl-5,6,8aα,9,10,11,12,12 aα,13,13aα-decahydro 8H-isoquino[2,1-g][1,6]naphthyridine;
2fluoro-12methanesulfonyl-5,6,8aα,9,10,11,12,-12aα,13,13aα-decahydro-8H-isoquino[2,1-g][1,6]naphthyridine;
3-fluoro-12-methanesulfonyl-5,6,8aα,9,10,11,12,-12aα,13,13aα-decahydro 8H-isoquino[2,1-g][1,6]naphthyridine;
12-aminosulfonyl-5,6,8aα,9,10,11,12,12aα,13,13aα-decahydro 8H-isoquino[2,1-g][1,6]naphthyridine;
3-methoxy-12-aminosulfonyl-5,6,8aα,9,10,11,12,-12aα,13,13aα-decahydro-8H-isoquino[2,1-g][1,6]naphthyridine;
12-methylaminosulfonyl-5,6,8aα,9,10,11,12,12aα, 13,13aα-decahydro-8H-isoquino[2,1-g][1,6]naphthyridine;
12-diethylaminosulfonyl-5,6,8aα,9,10,11,12,12aα,13,-13aα-decahydro-8H-isoquino[2,1-g][1,6]naphthyridine;
12-di-n-hexylaminosulfonyl-5,6,8aα,9,10,11,12,-12aα,13,13aα-decahydro-8H-isoquino[2,1-g][1,6]naphthyridine;
12-(1-piperazinosulfonyl)-5,6,8aα,9,10,11,12,-12aα,13,13aα-decahydro 8H-isoquino[2,1-g][1,6]naphthyridine;
12-(1-morpholinosulfonyl)-5,6,8aα,9,10,11,12, 12aα,13,13aα-decahydro 8H-isoquino[2,1-g][1,6]naphthyridine;
12-(1piperidinosulfonyl)-5,6,8aα,9,10,11,12,12aα,13,-13aα-decahydro-8H-isoquino[2,1-g][1,6]naphthyridine;
3-methyl-12-ethanesulfonyl-5,6,8aα,9,10,11,12, 12aα,13,13aα-decahydro-8H-isoquino[2,1-g][1,6]naphthyridine;
3-ethoxy-12-ethanesulfonyl-5,6,8aα,9,10,11,12,-12aα,13,13aα-decahydro 8H-isoquino[2,1-g][1,6]naphthyridine;
3-n-hexyloxy-12-ethanesulfonyl-5,6,8aα,9,10,11,12, 12aα,13,13aα-decahydro-8H-isoquino[2,1-g][1,6]naphthyridine;
2,3-diethoxy-12-ethanesulfonyl-5,6,8aα,9,10,11,12,-12aα,13,13aα-decahydro-8H-isoquino[2,1-g][1.6]naphthyridine;
3-methyl-12-(1-n hexanesulfonyl) 5,6,8aα,9,10,11, 12,12aα,13,13aα-decahydro 8H-isoquino[2,1-g][1,6]naphthyridine;
3-methoxy-12-(1-n-hexanesulfonyl)-5,6,8aα, 9,10,11,12,12aα,13,13aα-decahydro-8H-isoquino[2,1-g][1,6]naphthyridine;
2,3-dimethoxy-12-(1n-hexanesulfonyl)-5,6,8aα,9,10,11,12,12aα,13,13aα-decahydro-8H-isoquino[2,1-g][1,6]naphthyridine;
3methoxy-12phenylsulfonyl-5,6,8aα,9,10,11,12, 12aα,13,13aα-decahydro-8H-isoquino[2,1-g][1,6]naphthyridine;
3methoxy-12-(N,N-dimethylaminosulfonyl)-5,6,8aα,9,10,11,12,12aα,13,13aα-decahydro-8H-isoquino[2,1-g][1,6]naphthyridine; 11,12,12aα,13,-13aα-decahydro-8H-isoquino[2,1-g][1,6]naphthyridine;
2,3-dimethoxy-12-(N,N-dimethylaminosulfonyl)-5,6,8aα,9,10,11,12,12aα,13,13aα-decahydro-8H-isoquino [2,1-g][1,6]naphthyridine;

2,3-methylenedioxy-12-(N,N-dimethylaminosulfonyl)5,6,8aα,9,10,11,12,12aα,13,13aα-decahydro-8H-isoquino[2,1-g][1,6]naphthyridine;

2methyl-12-(2methoxymethanesulfonyl)-5,6,8aα,9,10,11,12,12aα,13,13aα-decahydro-8H-isoquino[2,1-g][1,6]naphthyridine;

12-N,N-dimethylaminocarbonyl-5,6,8aα,9,10,11,12,12aα,13,13aα-decahydro 8H-isoquino[2,1-g][1,6]naphthyridine;

12-N,N-diethylaminocarbonyl-5,6,8aα,9,10,11,12,12aα,13,13aα-decahydro-8H-isoquino[2,1-g][1,6]naphthyridine;

3-methoxy-12-N,N-dimethylaminocarbonyl-5,6,8aα,9,10,11,12,12aα,13,13aα-decahydro-8H-isoquino[2,1-g][1,6]naphthyridine;

2,3-methylenedioxy-12-N,N-dimethylaminocarbonyl-5,6,8aα,9,10,11,12,12aα,13,13aα-decahydro-8H-isoquino[2,1-g][1,6]naphthyridine;

2,3-methylenedioxy-12-N,N-dimethylaminocarbonyl-5,6,8a,9,10,11,12,12a,13,13a-decahydro-8H-isoquino[2,1-g][1,6]naphthyridine;

3-methoxy-12-(pyrrolidin-1-yl)carbonyl-5,6,8aα,9,10,11,12,12aα,13,13aα-decahydro-8H-isoquino[2,1-g][1,6]naphthyridine;

3-methoxy-12-(4-methylpiperazin-1-yl)carbonyl-5,6,8aα,9,10,11,12,12aα,13,13aα-decahydro-8H-isoquino[2,1-g][1,6]naphthyridine;

3-methoxy-12-(morpholin-1-yl)carbonyl-5,6,8aα,9,10,11,12,12aα,13,13aα-decahydro 8H-isoquino[2,1-g][1,6]naphthyridine;

3-methyl-12-N,N-dimethylaminocarbonyl-5,6,8aα,9,10,11,12,12aα,13,13aα-decahydro-8H-isoquino[2,1-g][1,6]naphthyridine;

2,3-dimethoxy-12-N,N-dimethylaminocarbonyl-5,6,8aα,9,10,11,12,12aα,13,13aα-decahydro-8H-isoquino[2,1-g][1,6]naphthyridine., 12-N-methyl-N-ethylaminocarbonyl-5,6,8aα,9,10,11,12,12aα,13,13aα-decahydro-8H-isoquino[2,1-g][1,6]naphthyridine;

12-N-methyl-N-butylaminocarbonyl-5,6,8aα,9,10,11,12,12aα,13,13aα-decahydro-8H-isoquino[2,1-g][1,6]naphthyridine;

12 N,N-di-n-hexylaminocarbonyl-5,6,8aα,9,10,11,12,12aα,13,13aα-decahydro-8H-isoquino[2,1-g][1,6]naphthyridine;

12 N,N-diphenylaminocarbonyl-5,6,8aα,9,10,11,12,12aα,13,13aα-decahydro-8H-isoquino[2,1-g][1,6]naphthyridine;

12-(pyrrolidin-1-yl)carbonyl-5,6,8aα,9,10,11,12,12aα,13,13aα-decahydro-8H-isoquino[2,1-g][1,6]naphthyridine;

12-(4methylpiperazin-1-yl)carbonyl-5,6,8aα,9,10,11,12,12aα,13,13aα-decahydro-8H-isoquino[2,1-g][1,6]naphthyridine;

12-(morpholin-1-yl)carbonyl-5,6,8aα,9,10,11,12,12aα,13,13aα-decahydro-8H-isoquino[2,1-g][1,6]naphthyridine;

3-methoxy-12-N-methyl-N-ethylaminocarbonyl-5,6,8aα,9,10,11,12,12aα,13,13aα-decahydro-8H-isoquino [2,1-g][1,6]naphthyridine;

3-methoxy-12-N-methyl-N-butylaminocarbonyl-5,6,8aα,9,10,11,12,12aα,13,13aα-decahydro-8H-isoquino[2,1-g][1,6]aphthyridine;

3-methoxy-12-N,N-di-n-hexylaminocarbonyl-5,6,8aα,9,10,11,12,12aα,13,13aα-decahydro 8H-isoquino [2,1-g][1,6]naphthyridine;

3-methoxy 12 N,N-diphenylaminocarbonyl-5,6,8aα,9,10,11,12,12aα,13,13aα-decahydro 8H-isoquino[2,1-g][1,6]naphthyridine;

2,3-methylenedioxy-12-N-methyl-N-ethylaminocarbonyl-5,6,8aα,9,10,11,12,12aα,13,13aα-decahydro-8H-isoquino [2,1-g][1,6]naphthyridine;

2,3-ethylenedioxy 12-N,N-dimethylaminocarbonyl-5,6,8aα,9,10,11,12,12aα,13,13aα-decahydro-8H-isoquino [2,1-g][1,6]naphthyridine;

2,3-methylenedioxy 12-N-methyl-N-butylaminocarbonyl-5,6,8aα,9,10,11,12,12aα,13,13aα-decahydro-8H-isoquino [2,1-g][1,6]naphthyridine;

2,3-methylenedioxy-12 N,N-di-n-hexylaminocarbonyl-5,6,8aα,9,10,11,12,12aα,13,13aα-decahydro 8H-isoquino [2,1-g][1,6]naphthyridine;

2,3-methylenedioxy 12 N,N-diphenylaminocarbonyl-5,6,8aα,9,10,11,12,12aα,13,13aα-decahydro 8H-isoquino [2,1-g][1,6]naphthyridine;

2,3-methylenedioxy-12-(pyrrolidin-1-yl)carbonyl-5,6,8aα,9,10,11,12,12aα,13,13aα-decahydro-8H-isoquino [2,1-g][1,6]naphthyridine;

2,3-methylenedioxy-12-(4 methylpiperazin-1-yl)-carbonyl-5,6,8aα,9,10,11,12,12aα,13,13aα-decahydro-8H-isoquino[2,1-g][1,6]naphthyridine;

2,3-methylenedioxy-12-(morpholin-1-yl)carbonyl-5,6,8aα,9,10,11,12,12aα,13,13aα-decahydro 8H-isoquino [2,1-g][1,6]naphthyridine;

2-methyl-12-N,N-dimethylaminocarbonyl 5,6,8aα,9,10,11,12,12aα,13,13aα-decahydro-8H-isoquino[2,1-g][1,6]naphthyridine;

2,3-dimethyl-12-N,N-dimethylaminocarbonyl-5,6,8aα,9,10,11,12,12aα,13,13aα-decahydro 8H-isoquino[2,1-g][1,6]naphthyridine;

3-n hexyl 12-N,N-dimethylaminocarbonyl-5,6,8aα,9,10,11,12,12aα,13,13aα-decahydro-8H-isoquino [2,1-g][1,6]naphthyridine;

2-methoxy-12-N,N-dimethylaminocarbonyl-5,6,8aα,9,10,11,12,12aα,13,13aα-decahydro-8H-isoquino[2,1-g][1,6]naphthyridine;

3-ethoxy 12-N,N-dimethylaminocarbonyl-5,6,8aα,9,10,11,12,12aα,13,13aα-decahydro-8H-isoquino [2,1-g][1,6]naphthyridine;

3n hexyloxy-12-N,N-dimethylaminocarbonyl-5,6,8aα,9,10,11,12,12aα,13,13aα-decahydro-8H-isoquino[2,1-g][1,6]naphthyridine;

3-hydroxy-12-N,N-dimethylaminocarbonyl-5,6,8aα,9,10,11,12,12aα,13,13aα-decahydro-8H-isoquino [2,1-g][1,6]naphthyridine;

3,4-methylenedioxy 12-N,N-dimethylaminocarbonyl-5,6,8aα,9,10,11,12,12aα,13,13aα-decahydro 8H-isoquino[2,1-g][1,6]naphthyridine;

3-chloro-12-N,N-dimethylaminocarbonyl 5,6,8aα,9,10,11,12,12aα,13,13aα-decahydro-8H-isoquino [2,1-g][1,6]naphthyridine;

3-fluoro-12-N,N-dimethylaminocarbonyl-5,6,8aα.9,10,11,12,12aα,13,13aα-decahydro 8H-isoquino[2,1-g][1,6]naphthyridine;

3-methoxy 12-[(R)-(+)-1phenylethylamino]carbonyl-5,6,8a,9,10,11,12,12a,13,13a-decahydro-8H-isoquino [2,1-g][1,6]naphthyridine;

13[(R)-(+) 1-phenylethylamino]carbonyl-5,6,8a,9,10,11,12,12a,13,13a decahydro-8H-isoquino[2,1-g][1,6]naphthyridine;

2,3-methylenedioxy-12-[(R) (+)-1-phenylethylamino]carbonyl-5,6,8a,9,10,11,12,12a,13,13a-decahydro-8H-isoquino[2,1-g][1,6]naphthyridine;

12-benzylaminocarbonyl 5,6,8aα,9,10,11,12,12aα, decahydro-8H-isoquino[2,1-g][1,6]naphthyridine;

12-isopropylaminocarbonyl-5,6,8aα,9,10,11,12,-12aα,13,13aα-decahydro-8H-isoquino[2,1-g][1,6]naphthyridine;

12-n-butylaminocarbonyl-5,6,8aα,9,10,11,12,12aα, 13,13aα-decahydro 8H-isoquino[2,1-g][1,6]naphthyridine;

12-t-butylaminocarbonyl-5,6,8aα,9,10,11,12,12aα, decahydro-8H-isoquino[2,1-g][1,6]naphthyridine;

3-methoxy-12-phenylaminocarbonyl-5,6,8aα,9,10,11,12,12aα,13,13aα-decahydro-8H-isoquino[2,1-g][1,6]naphthyridine;

12-[(R) (+)-1-phenylethylamino]carbonyl 5,6,8aα,9,10,11,12,12aα,13,13aα-decahydro-8H-isoquino [2,1-g][1,6]naphthyridine;

12-[(R)-(+)-1-phenylethylamino]-carbonyl-5,6,8aα, 9,10,11,12,12aα,13,13aα-decahydro-8H-isoquino 3-methoxy-12 [(R) (+) 1 phenylethylamino]carbonyl-9,10,11,12,12aα,13,13aα-decahydro-8H-isoquino[2,1-g][1,6]naphthyridine;

12-ethylaminocarbonyl-5,6,8aα,9,10,11,12,12aα,13,-13aα-decahydro-8H-isoquino[2,1-g][1,6]naphthyridine;

12-n-butylaminocarbonyl-5,6,8aα,9,10,11,12,-12aα,13,13aα-decahydro-8H-isoquino[2,1-g][1,6]naphthyridine;

12-n-octylaminocarbonyl 5,6,8aα,9,10,11,12,12aα,13,-13aα-decahydro 8H-isoquino[2,1-g][1,6]naphthyridine;

12-phenylaminocarbonyl 5,6,8aα,9,10,11,12,12aα, 13,13aα-decahydro-8H-isoquino[2,1-g][1,6]naphthyridine;

3-methoxy-12-ethylaminocarbonyl-5,6,8aα,9,10,11,12,12aα,13,13aα-decahydro-8H-isoquino[2,1-g][1,6]naphthyridine;

3-methoxy-12-n-butylaminocarbonyl-5,6,8aα,9,10,11,12,12aα,13,13aα-decahydro-8H-isoquino[2,1-g][1,6]naphthyridine;

3-methoxy 12-n-octylaminocarbonyl 5,6,8aα,9,10,11,12,12aα,13,13aα-decahydro-8H-isoquino[2,1-g][1,6]naphthyridine;

3-methoxy 12-phenylaminocarbonyl-5,6,8aα,9,10,11,12,12aα,13,13aα-decahydro-8H-isoquino[2,1-g][1,6]naphthyridine;

2,3-methylenedioxy-12-ethylaminocarbonyl-5,6,8aα, 9,10,11,12,12aα,13,13aα-decahydro 8H-isoquino [2,1-g][1,6]naphthyridine;

2,3-methylenedioxy-12-n butylaminocarbonyl 5,6,8aα,9,10,11,12,12aα,13,13aα-decahydro 8H-isoquino[2,1-g][1,6]naphthyridine;

2,3-methylenedioxy 12-n-octylaminocarbonyl-5,6,8aα,9,10,11,12,12aα,13,13aα-decahydro 8H-isoquino [2,1-g][1,6]naphthyridine;

2,3-methylenedioxy-12 phenylaminocarbonyl-5,6,8aα,9,10,11,12,12aα,13,13aα-decahydro 8H-isoquino[2,1-g][1,6]naphthyridine., 2,3-methylenedioxy 12-benzylaminocarbonyl 5,6,8aα, 9,10,11,12,12aα,13,13aα-decahydro-8H-isoquino[2,1-g][1,6]naphthyridine;

2-methyl-12benzylaminocarbonyl-5,6,8aα,9,10,11,12,12aα,13,13aα-decahydro 8H-isoquino[2,1-g][1,6]naphthyridine;

3-methyl 12-benzylaminocarbonyl-5,6,8aα,9,10,11,12,12aα,13,13aα-decahydro-8H-isoquino[2,1-g][1,6]naphthyridine;

2,3-dimethyl-12-benzylaminocarbonyl-5,6,8aα,9,10,11,12,12 aα,13,13aα-decahydro 8H-isoquino[2,1-g][1,6]naphthyridine;

3-n hexyl 12-benzylaminocarbonyl-5,6,8aα,9,10,11,12,12aα,13,13aα-decahydro-8H-isoquino[2,1-g][1,6]naphthyridine;

2-methoxy-12-benzylaminocarbonyl-5,6,8aα,9,10,11,12,12aα,13,13aα-decahydro-8H-isoquino[2,1-g][1,6]naphthyridine;

3-ethoxy-12-benzylaminocarbonyl-5,6,8aα,9,10,11,12,12aα,13,13aα-decahydro-8H-isoquino[2,1-g][1,6]naphthyridine;

3-n-hexyloxy-12-benzylaminocarbonyl-5,6,8aα,9,10,11,12,12aα,13,13aα-decahydro-b 8H-isoquino[2,1-g][1,6]naphthyridine;

3-hydroxy-12-benzylaminocarbonyl-5,6,8aα,9,10,11,12,12aα,13,13aα-decahydro-8H-isoquino[2,1-g][1,6]naphthyridine;

2,3-dimethoxy-12-benzylaminocarbonyl-5,6,8aα,9,10,11,12,12aα,13,13aα-decahydro-8H-isoquino[2,1-g][1,6]naphthyridine;

3,4 methylenedioxy-12-benzylaminocarbonyl-5,6,8aα,9,10,11,12,12aα,13,13aα-decahydro 8H-isoquino 2,1-g][1,6]naphthyridine;

3-chloro 12-benzylaminocarbonyl 5,6,8aα,9,10,11,12,12aα,13,13aα-decahydro 8H-isoquino[2,1-g][1,6]naphthyridine; and 3-fluoro 12-benzylaminocarbonyl-5,6,8aα,9,10,11,12,-12aα,13,13aα-decahydro-8H-isoquino[2,1-g][1,6]naphthyridine.

EXAMPLE 5

Preparation of (8aR,12aS,13aS)-3-methoxy-12-[(R)-(+)-phenylethylamino]carbonyl-5,6,8a,9,10,11,12,12a,13,13a-decahydro-8H-isoquino[2,1-g][1,6]naphthyridine and Related Compounds of Formula (I)

A. A solution of 11.5-g of (8aS,12aS,13aS) 3-methoxy 12-[(R)-(+)-1-phenylethylamino]carbonyl-5,6,8a,9,10,11,12,12a,13,13a decahydroisoquino[2,1-g][1,6]naphthyridin-8-one, in 50 ml of tetrahydrofuran was added slowly to a solution of 2.0-g of lithium aluminum hydride in 75 ml of tetrahydrofuran. The resulting mixture was stirred at reflux for 2 hours, cooled, and treated sequentially with 2.5 ml of water, 2.5 ml of 15% sodium hydroxide, and 7.5 ml of water. The mixture was filtered and the filtrate was evaporated to afford 8.8-g of (8aR,12aS,13aS) 3-methoxy 12-[(R)-(+)-1 phenylethylamino]carbonyl-5,6,8a,9,10,11,12,12a,13,-13a decahydro-8H-isoquino[2,1-g][1,6]naphthyridine, a compound of formula (I).

B. Similarly, replacing (8aS,12aS,13aS)-3-methoxy-12-[(R)-(+)-1-phenylethylamino]carbonyl-5,6,8a,9,10,11,12,12a,13,13a-decahydroisoquino[2,1-g][1,6]naphthyridin-8-one with other compounds of formula (3) and following the procedure in paragraph A above, the following compounds of formula (I) were prepared:

(8aR,12aS,13aS)-12-[(R)-(+)-1-phenylethylamino]-carbonyl -5,6,8a,9,10,11,12,12a,13,13a decahydro-8H-isoquino[2,1-g][1,6]naphthyridine; and (8aR,12aS,13aS)-2,3-methylenedioxy 12 [(R)-(+)-1-phenylethylamine]carbonyl 5,6,8a,9,10,11,12,-12a,13,13a-decahydro-8H-isoquino[2,1-g][1,6]naphthyridine.

C. Similarly, replacing (8aS,12aS,13aS) 3 methoxy 12-[(R)-(+)-1-phenylethylamino]carbonyl-5,6,8a,9,10,11,12,12a,13,13a-decahydroisoquino[2,1-g][1,6]naphthyridin-8-one with other compounds of formula (3), as the individual enantiomers or racemic or non-racemic mixtures thereof, and following the procedure in paragraph A above, any compounds of formula (I), as the individual enantiomers or racemic or non-racemic mixtures thereof, are prepared, in particular those named in Example 4 above.

What is claimed is:

1. A process for the preparation of a compound, as a single enantiomer or mixture of enantiomers, represented by the formula:

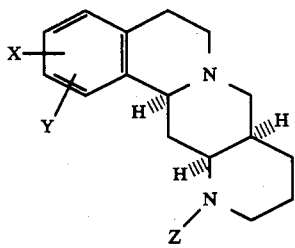

(IA)

wherein:

X and Y are independently hydrogen; hydroxy; lower alkyl of one to six carbon atoms; lower alkoxy of one to six carbon atoms; or halo; or X and Y when adjacent and taken together is methylenedioxy or ethylene-1,2-dioxy, and Z is —SO₂R, in which;

R is lower alkyl of one to six carbon atoms; phenyl optionally substituted by one or two substituents chosen from halo, amino, lower alkyl or one to four carbon atoms and lower alkoxy groups of one to four carbon atoms; —(CH₂)ₘOR¹; or —NR¹R²; wherein m is an integer of 1 to 6 and R¹ and R² are independently lower alkyl; or R¹ and R² taken together with the nitrogen to which they are attached represent a heterocycle of the formula:

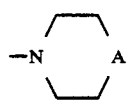

wherein A is —CH₂—, —NR¹— or oxygen;

which process comprises:

(A) contacting a compound of the formula:

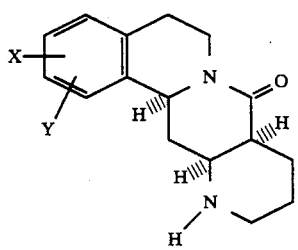

(2)

wherein X and Y are as defined above: with a compound of the formula RSO₂Cl or RSO₂Br;

where R is as defined above, to give a highly crystalline compound of the formula:

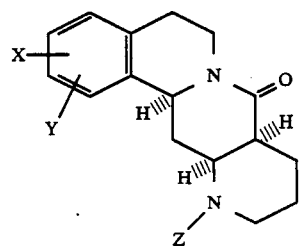

(3a)

wherein X, Y and Z are as defined above, followed by:

(B) contacting the compound of formula (3a) with a reducing agent chosen from the group consisting of lithium aluminum hydride, borane, triethyloxonium fluoroborate followed by sodium borohydride, sodium borohydride in the presence of a carboxylic etherate.

2. The process of claim 1, wherein the reducing agent is sodium borohydride in the presence of boron trifluoride etherate.

3. The process of claim 2, which is carried out in an ethereal solvent at an initial reaction temperature of about 0° to 20° C. followed by refluxing for between about 30 minutes and 1 hour, wherein the mole ratio of the compound of formula (18) to sodium borohydride is between about 1:3 to 1:5 and the mole ratio of the compound of formula (3) to boron trifluoride etherate is between about 1:5 to 1:7.

4. The process of claim 2, wherein the ethereal solvent is tetrahydrofuran, the initial reaction temperature is 10° C. followed by refluxing for 45 minutes, the mole ratio of the compound of formula (3) to sodium borohydride is 1:4 and the mole ratio of the compound of formula (3) to boron trifluoride etherate is 1:6.

5. The process of claim 4, wherein X is hydrogen or lower alkoxy and Y is hydrogen, or X and Y taken together is 2,3 methylenedioxy.

6. The process of claim 7, wherein R is lower alkyl.

7. The process of claim 6, wherein R is methyl.

8. The process of claim 2, wherein X is hydrogen or lower alkoxy and Y is hydrogen, or X and Y taken together is 2,3-methylenedioxy.

9. The process of claim 8, wherein R³ and R⁴ are lower alkyl of 1–4 carbon atoms.

10. The process of claim 9, wherein R³ and R⁴ are both methyl.

11. The process of claim 8, wherein R³ is hydrogen and R⁴ is phenyl lower alkyl.

12. The process of claim 11, wherein R⁴ is (R)-(+)-1-phenylethyl.

13. A compound, as a single enantiomer or mixture of enantiomers, represented by the formula:

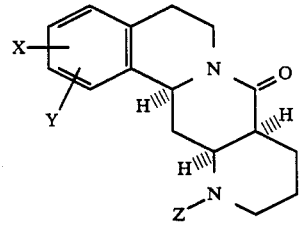

(3)

wherein

X and Y are independently hydrogen; hydroxy; lower alkyl of one to six carbon atoms; lower alkoxy of one to six carbon atoms; or halo; or X and Y when adjacent and taken together is methylenedioxy or ethylene-1,2-dioxy, and Z is —SO$_2$R or —C(O)NR$^3$R$^4$, in which., R is lower alkyl of one to six carbon atoms; phenyl optionally substituted by one or two substituents chosen from halo, amino, lower alkyl of one to four carbon atoms and lower alkoxy groups of one to four carbon atoms; —(CH$_2$)$_m$OR$^1$; of —NR$^1$R$^2$; wherein m is an integer of 1 to 6 and R$^1$ and R$^2$ are independently hydrogen or lower alkyl; and R$^3$ and R$^4$ are independently hydrogen; alkyl of one to eight carbon atoms; phenyl or phenyl lower alkyl in which any phenyl group may be optionally substituted by one or two substituents chosen from halo, lower; alkyl of one to four carbon atoms and lower alkoxy of one to four carbon atoms; or R$^1$ and R$^2$ taken together with the nitrogen to which they are attached or R$^3$ and R$^4$ taken together with the nitrogen to which they are attached represent a heterocycle of the formula;

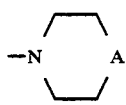

wherein A is —CH$_2$—, —NR$^1$— or oxygen.

14. The compound of claim 13, wherein Z is —wherein Z is —SO$_2$R.

15. The compound of claim 14, wherein R is lower alkyl.

16. The compound of claim 15, wherein R is methyl.

17. The compound of claim 16, wherein X is lower alkoxy and Y is hydrogen.

18. The compound of claim 17, wherein X is 3-methoxy, namely (±)-3-methoxy-12-methanesulfonyl-5,6,8aα,9,10,11,12,12aα,13,13α-decahydroisoquino-[2,1-g][1,6]naphthyridin-8 one.

19. A single enantiomer of the compound of claim 18, namely (8aS,12aS,13aS)-3-methoxy-12-methanesulfonyl-5,6,8a,9,10,11,12,12a,13,13a decahydroisoquino[2,1 g][1,6]naphthyridin-8one.

20. The compound of claim 16, wherein X and Y taken together is 2,3-methylenedioxy, namely (±) 2,3-methylenedioxy-12 methanesulfonyl-5,6,8aα,9,10,11,12,12aα,13,13α-decahydroisoquino[2,1g][1,6]-naphthyridin-8one.

21. A single enantiomer of the compound of claim 20, namely (8aS,12aS,13aS) 2,3methylenedioxy 12-methanesulfonyl-5,6,8a,9,10,11,12,12a,13,13a-decahydroisoquino[2,1-g][1,6]naphthyridin-8-one.

22. The compound of claim 12, wherein Z is —C(O)NR$^3$R$^4$.

23. The compound of claim 22, wherein X is hydrogen or lower alkoxy and Y is hydrogen, or X and Y taken together is 2,3-methylenedioxy.

24. The compound of claim 23, wherein R$^3$ and R$^4$ are lower alkyl of 1–4 carbon atoms.

25. The compound of claim 24, wherein R$^3$ and R$^4$ are both methyl.

26. The compound of claim 23, wherein R$^3$ is hydrogen and R$^4$ is phenyl lower alkyl.

27. The compound of claim 26, wherein R$^4$ is (R)-(±)-1-phenylethyl.

28. A process for the preparation of a compound, as a single enantiomer or mixture of enantiomers, represented by the formula:

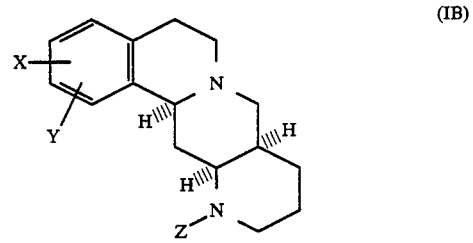

wherein:

X and Y are independently hydrogen; hydroxy; lower alkyl of one to six carbon atoms; lower alkoxy of one to six carbon atoms; or halo; or X and Y when adjacent and taken together is methylenedioxy or ethylene-1,2-dioxy, and Z is —C(O)NR$^3$R$^4$, in which;

R$^3$ and R$^4$ are independently hydrogen; alkyl of one to eight carbon atoms; phenyl or phenyl lower alkyl in which any phenyl group may be optionally substituted by one or two substituents chosen from halo, lower alkyl of one to four carbon atoms and lower alkoxy of one to four carbon atoms; or R$^3$ and R$^4$ taken together with the nitrogen to which they are attached represent a heterocycle of the formula:

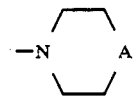

wherein A is —CH$_2$—, —N(lower alkyl)— or oxygen;

which process comprises:

(A) contacting a compound of the formula:

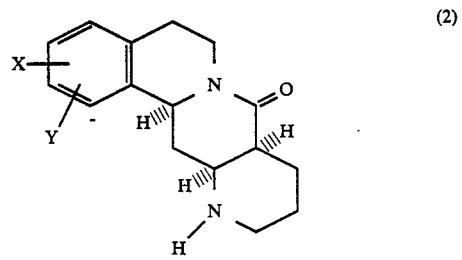

wherein X and Y are as defined above;
 (a) with a compound of the formula KNCO in the presence of acetic acid, or alternatively;
 (b) with a compound of the formula R$^4$NCO, or alternatively;
 (c) with a compound of the formula R$^3$R$^4$RCOCl;
where R$^3$ and R$^4$ are as defined above, to give a highly crystalline compound of the formula:

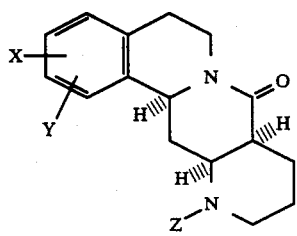

(3b)

wherein X Y and Z are as defined above, followed by:

(B) contacting the compound of formula (3b) with a reducing agent chosen from the group consisting of lithium aluminum hydride, borane, triethyloxonium fluoroborate followed by sodium borohydride, sodium borohydride in the presence of a carboxylic acid and sodium borohydride in the presence of boron trifluoride etherate.

29. The process of claim 28, wherein the reducing agent is sodium borohydride in the presence of boron trifluoride etherate.

* * * * *